(12) United States Patent
Schmidtchen et al.

(10) Patent No.: US 8,076,286 B2
(45) Date of Patent: Dec. 13, 2011

(54) ANTIMICROBIAL PEPTIDES AND USE THEREOF

(75) Inventors: Artur Schmidtchen, Lund (SE); Martin Malmsten, Taby (SE); Björn Walse, Lund (SE)

(73) Assignee: Dermagen AB, Lund (SE)

( * ) Notice: Subject to any disclaimer, the term of this patent is extended or adjusted under 35 U.S.C. 154(b) by 294 days.

(21) Appl. No.: 12/278,042

(22) PCT Filed: Feb. 12, 2007

(86) PCT No.: PCT/SE2007/000125
§ 371 (c)(1),
(2), (4) Date: Jan. 12, 2009

(87) PCT Pub. No.: WO2007/091959
PCT Pub. Date: Aug. 16, 2007

(65) Prior Publication Data
US 2009/0143299 A1    Jun. 4, 2009

Related U.S. Application Data

(60) Provisional application No. 60/772,378, filed on Feb. 10, 2006.

(30) Foreign Application Priority Data

Feb. 10, 2006 (SE) ........................ 0600307

(51) Int. Cl.
- *A01N 37/18* (2006.01)
- *A61K 38/00* (2006.01)
- *A61K 38/04* (2006.01)
- *A61P 31/04* (2006.01)
- *C07K 5/00* (2006.01)
- *C07K 7/00* (2006.01)
- *C07K 16/00* (2006.01)
- *C07K 17/00* (2006.01)

(52) U.S. Cl. .......... 514/2.4; 530/324; 530/325; 530/326

(58) Field of Classification Search .......... None
See application file for complete search history.

(56) References Cited

U.S. PATENT DOCUMENTS

| 5,618,675 A | 4/1997 | Larrick et al. |
|---|---|---|
| 5,646,014 A | 7/1997 | Hara |
| 5,717,064 A | 2/1998 | Julian et al. |
| 5,912,230 A | 6/1999 | Oppenheim et al. |
| 6,103,888 A * | 8/2000 | Larrick et al. ............... 536/23.5 |
| 6,495,516 B1 | 12/2002 | Little, II |
| 6,503,881 B2 | 1/2003 | Krieger et al. |
| 2003/0206938 A1 | 11/2003 | Pereira et al. |

FOREIGN PATENT DOCUMENTS

| CN | 1704431 | 12/2005 |
|---|---|---|
| WO | WO 97/31019 | 8/1997 |
| WO | WO 01/81578 | 11/2001 |
| WO | WO 02/36612 | 5/2002 |
| WO | WO 2004/016653 | 2/2004 |

OTHER PUBLICATIONS

Veronese. Peptide and protein PEGylation: a review of problems and solutions. Biomaterials, 2001. vol. 22, pp. 405-417.*
STN International, File Registry—Copyright 2007 ACS on STN RN 624009-74-1.
STN International, File Registry—Copyright 2007 ACS on STN RN 479861-65-9.
Niyonsaba et al. "Protective roles of the skin against infection: Implication of naturally occurring human antimicrobial agents β-defnsins, cathelicidin LL-37 and lyozyme." *J. of Dermatological Science*. vol. 40. 2005. pp. 157-168.
Lehrer et al. "Antimicrobial peptides in mammalian and insect host defence." *Innate Immunity*. vol. 11. 1999. pp. 3951-3959.
Boman. "Innate immunity and the normal microflora." *Immunological Reviews*. vol. 173. 2000. pp. 5-16.

* cited by examiner

*Primary Examiner* — Marcela M Cordero Garcia
(74) *Attorney, Agent, or Firm* — Merchant & Gould P.C.

(57) ABSTRACT

The invention relates to a molecule comprising at least the amino acid sequence $X_1\ X_2\ X_3\ X_4\ X_5\ X_6\ W\ X_8\ X_9\ X_{10}$ wherein $X_{4,6,9}$ is any amino acid residue, $X_1$ is I, L or V, $X_2$ is not C, $X_3$ is A, E, Q, R or Y, $X_5$ is not R, $X_8$ is I or L, $X_{10}$ is not H and wherein said molecule have a length of from about 10 to about 100 amino acid residues or an analogue thereof. The invention also relates to compositions comprising said molecule and use of the molecule and/or composition of the invention to combat microorganisms, such as bacteria, viruses, fungi, including yeast, and parasites.

20 Claims, 7 Drawing Sheets

ANTIMICROBIAL PEPTIDES AND USE THEREOF

This application is a National Stage Application of PCT/SE2007/000125, filed 12 Feb. 2007, which claims benefit of Serial No. 0600307-3, filed 10 Feb. 2006 in Sweden, and Ser. No. 60/772,378, filed 10 Feb. 2006 in the United States, and which applications are incorporated herein by reference. A claim of priority to all, to the extent appropriate, is made.

FIELD OF INVENTION

The invention relates to a molecule comprising at least the amino acid sequence $X_1 X_2 X_3 X_4 X_5 X_6 W X_8 X_9 X_{10}$ wherein $X_{4, 6, 9}$ is any amino acid residue, $X_1$ is I, L or V, $X_2$ is not C, $X_3$ is A, E, Q, R or Y, $X_5$ is not R, $X_8$ is I or L, $X_{10}$ is not H and wherein said molecule have a length of from about 10 to about 100 amino acid residues or an analogue thereof. The invention also relates to compositions comprising said molecule and use of the molecule and/or composition of the invention to combat microorganisms, such as bacteria, viruses, fungi, including yeast, and parasites.

BACKGROUND OF INVENTION

Several infections are successfully combated by the immune system of a mammal such as a human being. However, in some instances, bacteria, fungi, or viruses are not always cleared, which may cause localised or generalised acute infections. This is a serious concern at perinatal-, burn-, or intensive care units, and in immunocompromised individuals. In other cases, a continuous bacterial persistence at epithelial surfaces may cause or aggravate chronic disease. In humans, this is exemplified by chronic skin ulcers, atopic dermatitis and other types of eczema, acne, or genitourinary infections. For example, there is now considerable evidence that colonization or infection with the Gram-positive bacterium *Staphylococcus aureus* is a triggering or exacerbating factor in atopic dermatitis. Approximately 90% of all atopic dermatitis patients are colonized or infected by *S. aureus* whereas only 5% of healthy individuals harbour that bacterium Superantigens produced by the bacteria stimulate keratinocytes and T-lymfocytes, and trigger the inflammatory process. The inflammation leads to an impaired skin barrier function.

Symptomatic infections may be treated by various medicaments. Some diseases may also be combated by for instance vaccines. However, vaccines are not always the best treatment option and for certain microorganisms no vaccine is available. When no protection is available treatment of the disease is pursued. Often the treatment is performed by the use of an antibiotic agent, which kills the microbe. However, during the last years several microbes have become resistant against anti-biotic agents. Most likely, resistance problems will increase in the near future. Additionally, several individuals have developed allergy against the antibiotic agent, thereby reducing the possibility to effectively use certain antibiotic agents.

Epithelial surfaces of various organisms are continuously exposed to bacteria. During recent years the innate immune system, based on antibacterial peptides has been attributed important roles in the initial clearance of bacteria at biological boundaries susceptible to infection (Lehrer, R. I., and Ganz, T. (1999) *Curr Opin Immunol* 11: 23-27, Boman, H. G. (2000) *Immunol. Rev.* 173, 5-16). Molecules kill bacteria by permeating their membranes, and thus the lack of a specific molecular microbial target minimises resistance development.

Several peptides and proteins, unrelated to the herein, described peptides are known in the art.

U.S. Pat. No. 6,503,881 disclose cationic peptides being an indolicidin analogue to be used as a molecule. The cationic peptides being derived from different species, including animals and plants.

U.S. Pat. No. 5,912,230 disclose anti-fungal and anti-bacterial histatin-based peptides. The peptides being based on defined portions of the amino acid sequences of naturally occurring human histatins and methods for treatment of fungal and bacterial infections.

U.S. Pat. No. 5,717,064 disclose methylated lysine-rich lytic peptides. The lytic peptides being tryptic digestion resistant and non-natural. The lytic peptides are suitable for in vivo administration.

U.S. Pat. No. 5,646,014 disclose a peptide. The peptide was isolated from an antimicrobial fraction from silkworm hemolymph. The peptide exhibits excellent antimicrobial activity against several bacterial strains, such as *Escherichia coli, Staphylococcus aureus* and *Bacillus cereus*.

WO2004016653 discloses a peptide based on the 20-44 sequence of azurocidin. This peptide contains a loop structure linked by disulfide bridges.

U.S. Pat. No. 6,495,516 and related patents, disclose peptides based on the bactericidal 55 kDa protein bactericidal/permeability increasing protein (BPI). The peptides exerted antimicrobial effects as well as had LPS-neutralising capacity.

WO 01/81578 discloses numerous sequences encoding G-coupled protein-receptor related polypeptides, which may be used for numerous diseases.

At present, over 700 different peptide sequences are known (www.bbcm.univ.trieste.it/~tossi/search.htm), including cecropins, defensins magainins and cathelicidins.

Even though there are a relatively large number of peptides available today there is still an increased need of new improved peptides, which can be used to combat microbes, microbes which are resistant or tolerant against antibiotic agents and/or other antimicrobial agents. More importantly, there is a need for new molecules, which are non-allergenic when introduced into mammals such as human beings. Bacteria have encountered endogenously produced molecules during evolution without induction of significant resistance.

SUMMARY OF THE INVENTION

According to a first embodiment the invention relates to a molecule comprising at least the amino acid sequence $X_1 X_2 X_3 X_4 X_5 X_6 W X_8 X_9 X_{10}$ wherein $X_{4, 6, 9}$ is any amino acid residue, $X_1$ is I, L or V, $X_2$ is not C, $X_3$ is A, E, Q, R or Y, $X_5$ is not R, $X_8$ is I or L, $X_{10}$ is not H and wherein said molecule have a length of from about 10 to about 100 amino acid residues or an analogue thereof.

According to a second embodiment the invention relates a composition comprising at least one molecule as defined above.

According to a third embodiment the invention relates to a product comprising said molecule and/or said composition.

According to a fourth embodiment the invention relates to the use of said molecule for use in medicine.

According to a fifth embodiment the invention relates to the use of said molecule or said composition for the manufacturing of an antimicrobial composition for reduction and/or elimination of microorganisms to treat or prevent a microbial infection.

Finally, the invention relates to a method to reduce and/or eliminate microorganisms to treat and/or prevent a disease and/or disorder comprising a microbial infection by use of a molecule(s) as defined above or a composition or a product as defined above, comprising administering to a mammal a therapeutically effective amount of an pharmaceutical composition comprising molecule or molecules of the invention.

By providing such molecules, the risks for allergic reactions to molecules may be reduced due to the fact that the molecules are derived from the polypeptide sequence of endogenous proteins and/or peptides. By using short peptides the stability of the peptide is increased and the production costs reduced, as compared to longer peptides and proteins, whereby the invention may be economically advantageous. Furthermore short peptides, in contrast to longer polypeptides, may easily be prepared using synthetic methods known in the art, such as solid phase synthesis. In contrast to longer polypeptides, which easily are denatured, short peptides are more stable. Due to this fact, use of such short peptides to manufacture medical compositions put less restrictions of other components to be used in said medical composition in terms of conserved activity.

The peptides of the invention provide compositions, which facilitate efficient prevention, reduction or elimination of microorganisms. Thereby the possibility to combat microorganisms, which are resistant or tolerant against current antibiotic agents, may be increased. Moreover, mammals, which are allergic against commercially available antimicrobial agents, may be treated and the molecule is not toxic for the mammal to be treated. By providing pharmaceutical compositions, which are derived from endogenous improved proteins, the probability may be reduced or even eliminated that a mammal will develop allergy against these particular peptides. This makes the pharmaceutical compositions useful for several applications in which the pharmaceutical compositions contact a mammal either as a medicament or as an additive to prevent infections.

Additionally, the use of short peptides may improve bioavailability. Furthermore, the use of structurally distinct peptides with specific or preferable actions on Gram-negative and Gram-positive bacteria, or fungi, enables specific targeting of various microorganisms, thus minimising development of resistance and ecological problems. By using supplementing peptides, which are comparable to peptides already existing in the mammal, the risk of additional ecological pressure by novel antibiotics is further diminished. Finally, these formulations may also enhance the effect of endogenous molecules.

Accordingly the invention relates to new molecules having improved properties and which solves a number of problems defined wherein a subset are mentioned within the application.

Additionally the invented molecules are stable in the physiological environment within the mammal, i.e., is active and does not degrade or will not be degraded by any proteases. During an infection caused by a microorganism, a number of systems in the mammal and microorganism are activated such as different proteases. One example being the neutrophil elastase. Additionally the molecule of the invention should still be active against different microorganisms, such as Gram negative bacteria, such as *P. aeruginosa*, when the molecule is dissolved in physiological salt, mimicking the environment of a human being.

Accordingly, the preferential cell-lysis activity of (antimicrobial) peptides is one feature of interest since Eukaryotic cell lysis occurs at higher concentrations of most known (antimicrobial) peptides as compared with the concentrations needed for lysis of micro-organisms. It is therefore in certain circumstances interesting that the peptides possess a low level of mammalian cell membrane activity as measured by e.g. haemolytic potential, when considering certain clinical indications. Examples of indications are but not limited to conjunctivitis, keratitis, otitis media, etc. On the other hand for some other indication it might be of interest that the peptides initiate a certain level of mammalian membrane targeting activity (which means having a higher degree of hemolysis) to trigger e.g. wound healing activity, immunological defense mechanisms, initiation of vascularisation (angiogenesis), prevention of vascularisation (anti-angiogenesis), etc. A high degree of membrane activity, as measured by e.g. haemolysis, may thus enable the peptides to have therapeutic potential in selected indications, i.e., peptides having both a high activity as well as low activity are of interest depending on what the peptide should be used for. Hemolysis may be blocked or attenuated in physiological environments, such as human plasma or wound fluid. Thus, by varying the peptide toxicity in vitro, a series of templates are generated for putative therapeutic applications in vivo.

The inventive molecules increase the list of antimicrobial agents, which aid in the choice to prevent, reduce or eliminate microorganisms in all kind of applications including but not limited to those that invade or infect mammals, such as the human being.

DETAILED DESCRIPTION OF THE INVENTION

Definitions

Figure 1A:
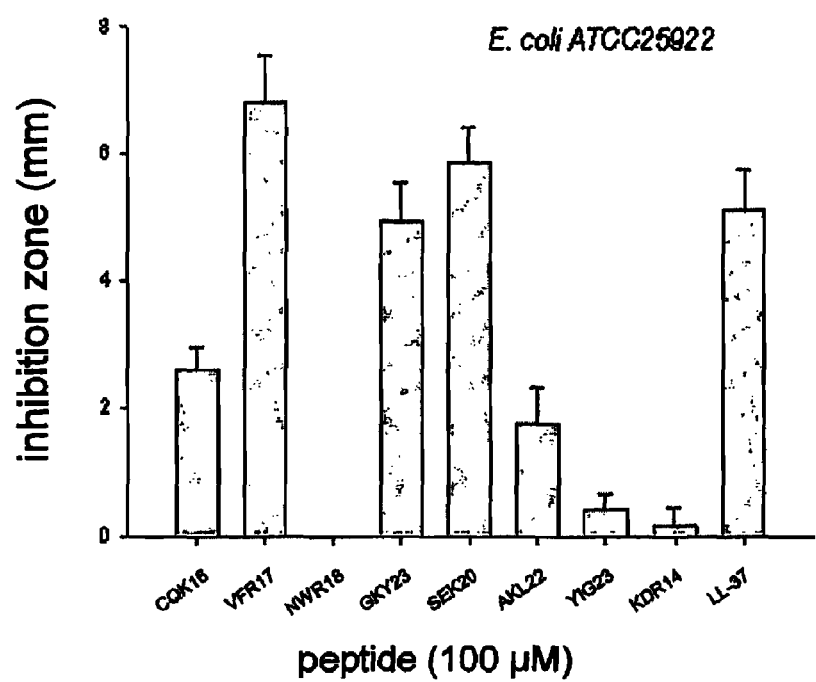
FIG. 1 *a-e* Antibacterial activities of peptides of coagulation factors. Inhibitory effects of the peptides were visualized as zones of bacterial clearance in RDA, and are indicated on the y-axis (in mm).
Figure 1B:
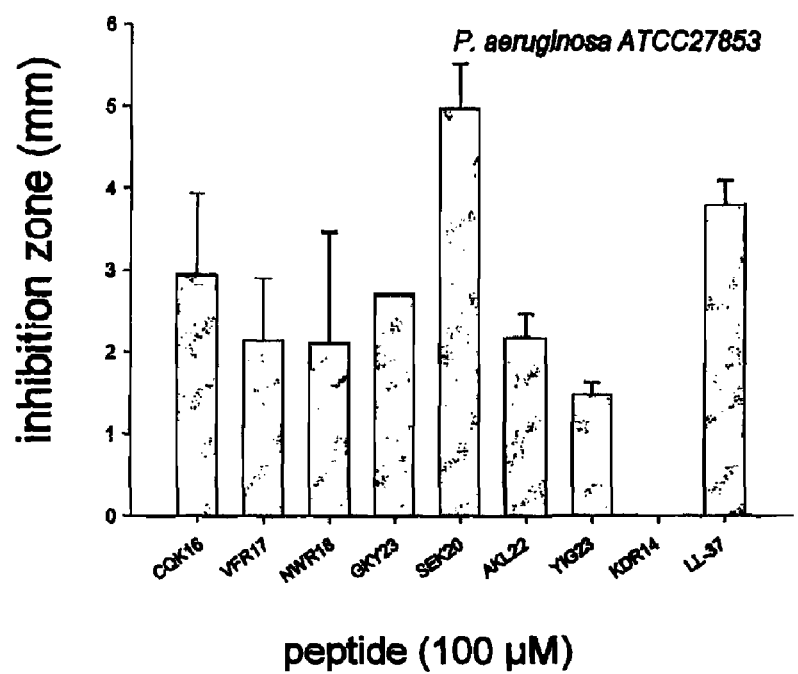
Figure 1C:
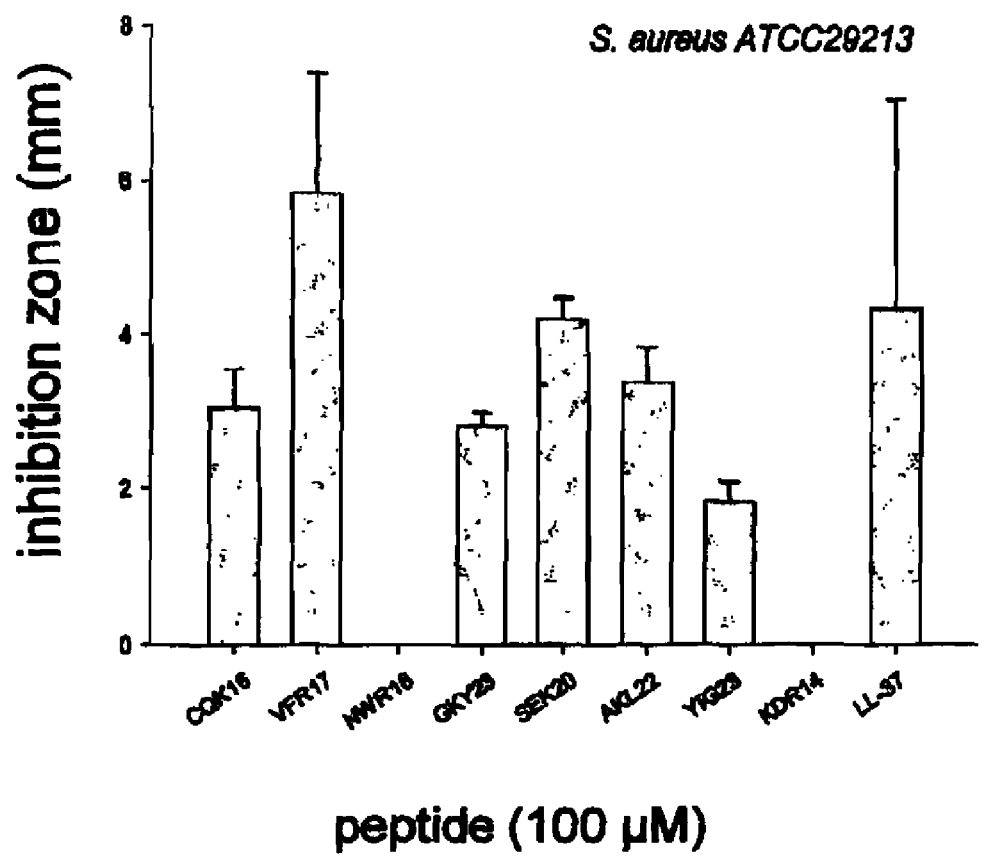
Figure 1D:
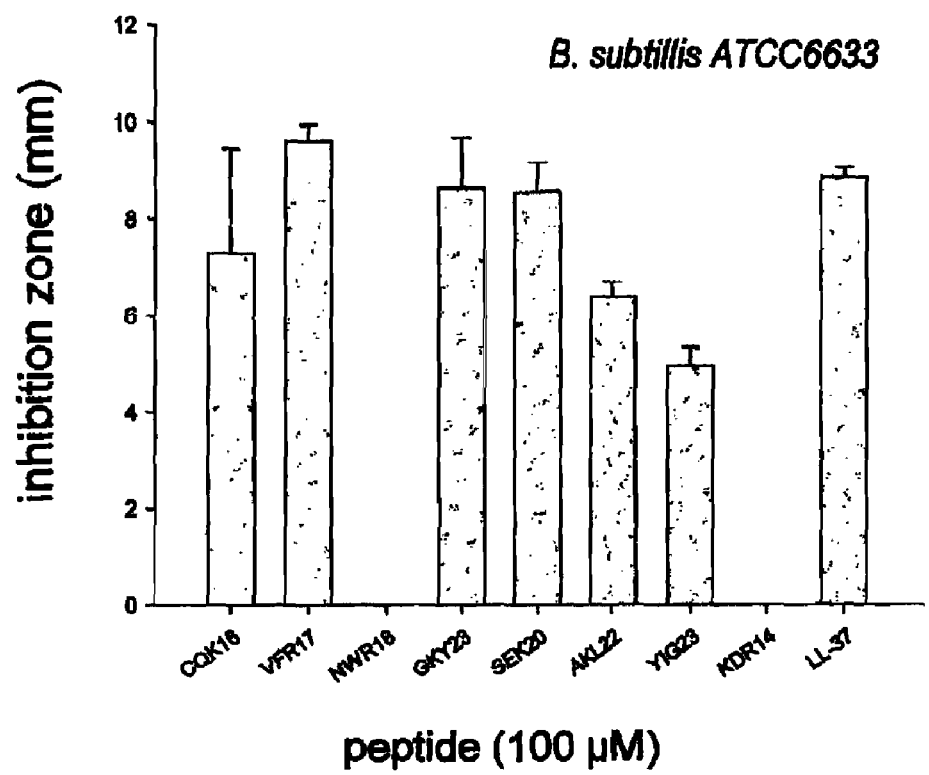
Figure 1E:
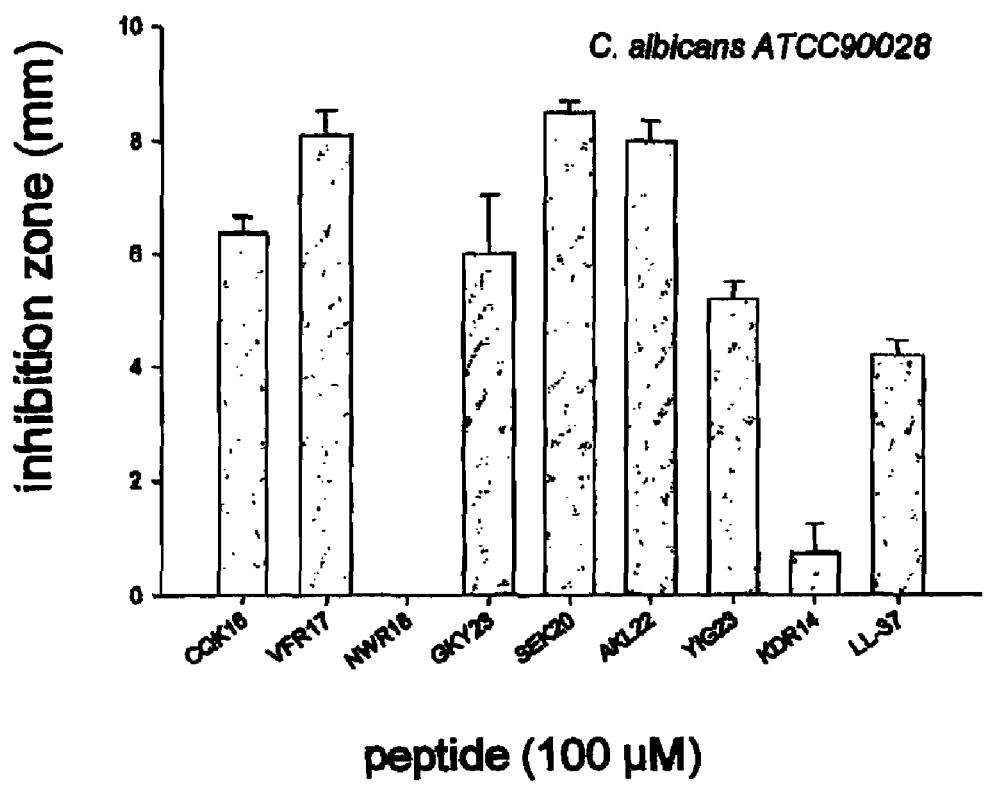

In the context of the present application and invention the following definitions apply:

The term "nucleotide sequence" is intended to mean a sequence of two or more nucleotides. The nucleotides may be of genomic DNA, cDNA, RNA, semi-synthetic or synthetic origin or a mixture thereof. The term includes single and double stranded forms of DNA or RNA.

The term "antimicrobial composition" is intended to mean any composition containing the invented peptides according to the invention, such as pharmaceutical compositions useful to combat microorganisms, which attack mammals as well as compositions comprising one or more additional antimicrobial agents such as anti-biotics as well as other agents.

The term "substituted" is intended to mean that an amino acid residue is replaced by another amino acid residue. For example, F2K means that the phenylalanin amino acid residue in position number 2 in SEQ ID NO:2 has been substituted, i.e., replaced by lysine.

The term "analogues thereof" is intended to mean that part of or the entire polypeptide of SEQ ID NO: 1 is based on non protein amino acid residues, such as aminoisobutyric acid (Aib), norvaline gamma-aminobutyric acid (Abu) or ornithine Examples of other non protein amino acid residues can be found at www.hort.purdue.edu/rhodcv/hort640c/polyam/po00008.htm.

The term "removed" is intended to mean that at least one amino acid residue has been removed, i.e., released from the polypeptide without being replaced by another amino acid residue.

The term "sequence identity" indicates a quantitative measure of the degree of homology between two amino acid sequences or between two nucleic acid sequences of equal length. If the two sequences to be compared are not of equal length, they must be aligned to give the best possible fit, allowing the insertion of gaps or, alternatively, truncation at the ends of the polypeptide sequences or nucleotide sequences. The sequence identity can be calculated as $$\frac{(N_{ref} - N_{dif})100}{N_{ref}},$$

wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}=2$ and $N_{ref}=8$). A gap is counted as non-identity of the specific residue(s), i.e. the DNA sequence AGTGTC will have a sequence identity of 75% with the DNA sequence AGTCAGTC ($N_{dif}=2$ and $N_{ref}=8$).

With respect to all embodiments of the invention relating to amino acid sequences, the percentage of sequence identity between one or more sequences may also be based on alignments using the clustal W software (www.ebi.ac.uk/clustalW/index.html) with default settings.

The term "molecule" is intended to mean a peptide, which prevents, inhibits, reduces or destroys a microorganism. The antimicrobial activity can be determined by any method, such as the method in EXAMPLE 3. The term "molecule" is also intended to mean a peptide with or without modification such as substitutions, chemical modifications such as esterification.

The term "amphipathic" is intended to mean the distribution of hydrophilic and hydrophobic amino acid residues along opposing faces of an α-helix structure, β-strand, linear, circular, or other secondary conformation, as well as along opposing ends of the peptide primary structure, which result in one face or end of the molecule being predominantly charged and hydrophilic and the other face or end being predominantly hydrophobic. The degree of amphipathicity of a peptide can be assessed, e.g., by plotting the sequence of amino acid residues by various web-based algorithms, eg. those found on us.expasy.org/cgi-bin/protscale.pl or www.mbio.ncsu.edu/BioEdit/bioedit.html. The distribution of hydrophobic residues can be visualised by helical wheel diaGrams. Secondary structure prediction algorithms, such as GORIV and AGADIR can be found at www.expasv.com.

The term "cationic" is intended to mean a molecule, which has a net positive charge within the pH range of from about 2 to about 12, such as within the range from about 4 to about 10.

The term "microorganism" is intended to mean any living microorganism. Examples of microorganisms are bacteria, fungus, virus, parasites and yeasts.

The term "antimicrobial agent" is intended to mean any agent, which prevent, inhibit or destroy life of microbes. Examples of antimicrobial agents can be found in The Sanford Guide to Antimicrobial Therapy (32nd edition, Antimicrobial Therapy, Inc, US).

In the present context, amino acid names and atom names are used as defined by the Protein DataBank (PDB) (www.p-db.org), which is based on the IUPAC nomenclature (IUPAC Nomenclature and Symbolism for Amino Acids and Peptides (residue names, atom names etc.), Eur J. Biochem., 138, 9-37 (1984) together with their corrections in Eur J. Biochem., 152, 1 (1985). The term "amino acid" is intended to indicate an amino acid from the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W) and tyrosine (Tyr or V), or derivatives thereof.

DESCRIPTION

Molecule

The invention relates to peptides having antimicrobial activity and having an amino acid sequence being derived from one or more coagulation proteins. The coagulation factors thrombin (factor II), factor VII, factor IX, factor X, factor XI, factor XII, protein C and plasma kallikrein belong to the peptidase S1 family originating from the superfamily of trypsin-like serine proteases. They consist of a heterodimer of a light chain and a heavy chain linked by a disulfide bond. The heavy chain contains the peptidase S1 domain, which is folded into two domains each arranged as a six-stranded antiparallel β-barrel. The carboxy terminus of all these proteins ends with an α-helix (data not shown). It has been found that peptides derived from this α-helical carboxy terminal part of the protein possess anti-bacterial properties. In addition, peptides derived from an exposed disulfide bonded loop approximately 55 residues further amino terminal of the carboxy terminal α-helix also display antibacterial properties. The protein sequences for these regions of the peptidases are highly conserved.

The invention relates to a new invented molecule comprising at least the amino acid sequence

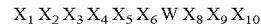

wherein
$X_{4, 6, 9}$ is any amino acid residue
$X_1$ is I, L or V
$X_2$ is not C
$X_3$ is A, E, Q, R or Y
$X_5$ is not R
$X_8$ is I or L
$X_{10}$ is not H
and wherein said molecule have a length of from about 10 to about 100 amino acid residues or an analogue thereof. such as a molecule comprises the amino acid sequence shown in SEQ ID NO:2 or, wherein said molecule differs from the amino acid sequence shown in SEQ ID NO:2 in that at least one amino acid residue selected from the group consisting of V1L, V1I, F2K, F2T, I8L, Q9R and Q9K has been substituted. The term "analogue" being defined above. Peptides containing such a motif have an amino acid composition giving a subtle interplay of structuring, charge, amphipathicity and hydrophobicity such that the petides possess anti-bacterial activity. In particular, the antimicrobial potency is related to the inducibility of an α-helical conformation in a membrane-mimicking environment, rather than intrinsic helical stability. One example being a molecule which differs from the amino acid sequence shown in SEQ ID NO:2 in that at least one amino acid residue selected from the group consisting of V1L, F2K, I8L, Q9R and Q9K has been substituted. The molecule may for example be a peptide being derived from the C-terminal part of an endogenous polypeptides, such as terminating between 4 to 24 amino acid residues from the C-terminal end.

The new invented molecule may be used to combat microorganisms, such as bacteria, viruses, fungi, including yeast, and parasites and solves the above defined problems. The molecule may have a length of from about 10 to about 50 amino acid residues, such as 10 to about 35 amino acid residues. Examples are a length of 10, 11, 12, 13, 14, 15, 16, 17, 18, 19, 20, 21, 22, 23, 24, 25, 26, 27, 28, 29, 30, 31, 32, 33, 34 or 35 amino acid residues. A turn in an α-helix requires 3.6 amino acid residues and thus peptides of ten or more amino acid residues should be able to form at least three turns of an α-helix yielding the necessary framework for an anti-bacterial peptide.

The invention also relates to a molecule comprising at least the amino acid sequence $$X_1 X_2 X_3 X_4 X_5 X_6 W X_8 X_9 X_{10} X_{11} X_{12} X_{13}$$

wherein
$X_{4, 6, 9, 11}$ is any amino acid residue
$X_1$ is I, L or V
$X_2$ is not C
$X_3$ is A, E, Q, R or Y
$X_5$ is not R
$X_8$ is I or L
$X_{10}$ is not H
$X_{12}$ is I, M or T
$X_{13}$ is D, K, Q or R
and wherein said molecule has a length of from about 20 to about 100 amino acid residues or a molecule comprising at least the amino acid sequence $$X_1 X_2 X_3 X_4 X_5 X_6 W X_8 X_9 X_{10} X_{11} X_{12} X_{13} X_{14} X_{15} X_{16} X_{17}$$

wherein
$X_{4, 6, 9, 11, 14, 15}$ is any amino acid residue
$X_1$ is I, L or V
$X_2$ is not C
$X_3$ is A, E, Q, R or Y
$X_5$ is not R
$X_8$ is I or L
$X_{10}$ is not H
$X_{12}$ is I, M or T
$X_{13}$ is D, K, Q or R
$X_{16}$ is G or D
$X_{17}$ is E, L, G, R or K
and wherein said molecule has a length of from about 20 to about 100 amino acid residues.

Accordingly, the invention relates to a molecule comprising the amino acid sequence shown in SEQ ID NO:1 or, wherein said molecule differs from the amino acid sequence shown in SEQ ID NO:1 in that at least one amino acid residue selected from the group consisting of V1L, V1I, F2K, F2T, I8L, Q9R, Q9K, I12T, D13K, D13R, Q14L, Q14I, E17K and E17R has been substituted and wherein E17 optionally has been deleted, such as a molecule that differs from the amino acid sequence shown in SEQ ID NO:1 in that at least one amino acid residue selected from the group consisting of V1L, F2K, I8L, Q9R, Q9K, I12T, D13K, D13R, E17K and E17R has been substituted and wherein E17 optionally has been deleted. Examples of molecules are found in SEQ ID NO:3-49.

The molecule according to the second aspect may have a length of from about 17 to about 50 amino acid residues, such as a length of from about 17 to about 35 amino acid residues. Examples are a length of 17, 18, 19, 20, 21, 22, 23, 24, 25, 26, 27, 28, 29, 30, 31, 32, 33, 34 or 35 amino acid residues.

Additionally the peptide may be substituted in one or more amino acid residues, such as from 2-21 amino acid residues. For example 1, 2, 3, 4, 5, 6, 7, 8, 9, 10, 11, 12, 13, 14, 15, 16, 17, 18, 19 amino acid residues may be removed and/or substituted.

The peptides may be derived from endogenous human peptides as well as being synthetic or semisynthetic.

One or more amino acid residues may be removed and/or substituted as long as the antimicrobial activity remains as well as the stability of the invented peptides.

The molecules may be extended by one or more amino acid residues, such as 1-100 amino acid residues, 10-50 amino acid residues, 5-50 amino acid residues or 6, 7, 8, 9, 10, 11, 12, 13, 14, 15, 16, 17, 18, 19, 20, 21, 22, 23, 24, 25, 26, 27, 28, 29 or 30 amino acid residues. Such additional amino acids may duplicate a sequence contiguous to the sequence of the molecule derived from a non-antimicrobial protein. The number to be added depends on which microorganism to be combated in including, stability of the peptide, toxicity, the mammal to be treated or in which product the peptide should be in and which peptide structure the molecule is based upon. The number of amino acid residues to be added to the peptides depends also on the choice of production, e.g., expression vector and expression hosts and the choice of manufacturing the pharmaceutical composition. The extension may be at the N- or C-terminal part or at both parts of the molecules as long as it does not disrupt the antimicrobial effect of the peptide. The molecules may also be a fusion protein, wherein the molecule is fused to another peptide.

Additionally the molecules may be operably linked to other known molecules or other substances, such other peptides, lipids, proteins, oligosaccharides, polysaccharides, other organic compounds, or inorganic substances. For example the molecules may be coupled to a substance which protect the molecules from being degraded within a mammal prior to the molecules has inhibited, prevented or destroyed the life of the microorganism.

Accordingly the molecules may be modified at the C-terminal part by amidation or esterification and at the N-terminal part by acylation, acetylation, PEGylation, alkylation and the like.

The molecules may be obtained from a naturally occurring source, such as from a human cell, a c-DNA, genomic clone, chemically synthesised or obtained by recombinant DNA techniques as expression products from cellular sources.

The molecules may be synthesised by standard chemical methods, including synthesis by automated procedure. In general, peptide analogues are synthesised based on the standard solid-phase Fmoc protection strategy with HATU (N-[DIMETHYLAMINO-1H-1,2,3,-TRIAZOLO[4,5-B]PYRIDIN-1-YLMETHYLELE]-N-METHYLMETHANAMINIUM HEXAFLUOROPHOSPHATE N-OXIDE) as the coupling agent or other coupling agents such as HOAt-1-HYDROXY-7-AZABENZOTRIAZOLE. The peptide is cleaved from the solid-phase resin with trifluoroacetic acid containing appropriate scavengers, which also deprotects side chain functional groups. Crude peptide is further purified using preparative reversed-phase chromatography. Other purification methods, such as partition chromatography, gel filtration, gel electrophoresis, or ion-exchange chromatography may be used. Other synthesis techniques, known in the art, such as the tBoc protection strategy, or use of different coupling reagents or the like can be employed to produce equivalent peptides.

Peptides may alternatively be synthesised by recombinant production (see e.g., U.S. Pat. No. 5,593,866). A variety of host systems are suitable for production of the peptide analogues, including bacteria, such as *E. coli*, yeast, such as *Saccharomyces cerevisiae* or *pichia*, insects, such as Sf9, and mammalian cells, such as CHO or COS-7. There are many expression vectors available to be used for each of the hosts and the invention is not limited to any of them as long as the vector and host is able to produce the molecule. Vectors and procedures for cloning and expression in *E. coli* can be found in for example Sambrook et al. (Molecular Cloning.: A Laboratory Manual, Cold Spring Harbor Laboratory Press, Cold Spring Harbor, N.Y., 1987) and Ausubel et al. (Current Protocols in Molecular Biology, Greene Publishing Co., 1995).

Finally, the peptides may be purified from plasma, blood, various tissues or the like. The peptides may be endogenous, or generated after enzymatic or chemical digestion of the purified protein. For example, a protein may be digested by trypsin and the resulting antibacterial peptides further isolated in larger scale.

A DNA sequence encoding the molecule is introduced into a suitable expression vector appropriate for the host. In preferred embodiments, the gene is cloned into a vector to create a fusion protein. To facilitate isolation of the peptide sequence, amino acids susceptible to chemical cleavage (e.g., CNBr) or enzymatic cleavage (e.g., V8 protease, trypsin) are used to bridge the peptide and fusion partner. For expression in *E. coli*, the fusion partner is preferably a normal intracellular protein that directs expression toward inclusion body formation. In such a case, following cleavage to release the final product, there is no requirement for renaturation of the peptide. In the present invention, the DNA cassette, comprising fusion partner and peptide gene, may be inserted into an expression vector. Preferably, the expression vector is a plasmid that contains an inducible or constitutive promoter to facilitate the efficient transcription of the inserted DNA sequence in the host.

The expression vector can be introduced into the host by conventional trans-formation techniques such as by calcium-mediated techniques, electroporation, or other methods well known to those skilled in the art.

The sequence encoding the molecule may be derived from a natural source such as a mammalian cell, an existing cDNA or genomic clone or synthesised. One method, which may be used, is amplification of the molecule by the aid of PCR using amplification primers which are derived from the 5' and 3' ends of the antimicrobial DNA template and typically incorporate restriction sites chosen with regard to the cloning site of the vector. If necessary, translational initiation and termination codons can be engineered into the primer sequences. The sequence encoding the molecule may be codon-optimised to facilitate expression in the particular host as long as the choice of the codons are made considering the final mammal to be treated. Thus, for example, if the molecule is expressed in bacteria, the codons are optimised for bacteria.

The expression vector may contain a promoter sequence, to facilitate expression of the introduced molecule. If necessary, regulatory sequences may also be included, such as one or more enhancers, ribosome binding site, transcription termination signal sequence, secretion signal sequence, origin of replication, selectable marker, and the like. The regulatory sequences are operably linked to each other to allow transcription and subsequent translation. If the molecule is to be expressed in bacteria, the regulatory sequences are those which are designed to be used within bacteria and such are well-known for a person skilled in the art. Suitable promoters, such as constitutive and inducible promoters, are widely available and includes promoters from T5, T7, T3, SP6 phages, and the trp, lpp, and laci operons.

If the vector containing the molecule is to be expressed within bacteria examples of origin are either those, which give rise to a high copy number or those which give rise to a low copy, for example f1-ori and col E1 ori.

Preferably, the plasmids include at least one selectable marker that is functional in the host, which allows transformed cells to be identified and/or selectively grown. Suitable selectable marker genes for bacterial hosts include the ampicillin resistance gene, chloramphenicol resistance gene, tetracycline resistance gene, kanamycin resistance gene and others known in the art.

Examples of plasmids for expression in bacteria include the pET expression vectors pET3a, pET 11a, pET 12a-c, and pET 15b (available from Novagen, Madison, Wis.). Low copy number vectors (e.g., pPD100) can be used for efficient overproduction of peptides deleterious to the *E. coli* host (Dersch et al., FEMS Microbiol. Lett. 123:19, 1994).

Examples of suitable hosts are bacteria, yeast, insects and mammal cells. However, often either bacteria such as *E. coli* is used.

The expressed molecule is isolated by conventional isolation techniques such as affinity, size exclusion, or ionic exchange chromatography, HPLC and the like. Different purification techniques can be found in A Biologist's Guide to Principles and Techniques of Practical Biochemistry (eds. Wilson and Golding, Edward Arnold, London, or in Current Protocols in Molecular Biology (John Wiley & Sons, Inc).

Accordingly, the molecules may bind and inactivate lipopolysaccharides from various Gram-negative bacteria, thus acting as inhibitors of lipopolysaccharide-induced inflammation. The molecules may also modulate growth of eukaryotic cells.

Additionally, the invention relates to a composition comprising said molecule or a pharmaceutical compositions comprising a molecule as described above and a pharmaceutical acceptable buffer, diluent, carrier, adjuvant or excipient. Additional compounds may be included in the compositions, such as other molecules. Examples of other molecules are disclosed in WO 2005/061535 and WO 2005/001737. Other examples include, chelating agents such as EDTA, EGTA or glutathione. The pharmaceutical compositions may be prepared in a manner known in the art that is sufficiently storage stable and suitable for administration to humans and animals. The pharmaceutical compositions may be lyophilised, e.g., through freeze drying, spray drying or spray cooling.

"Pharmaceutically acceptable" means a non-toxic material that does not decrease the effectiveness of the biological activity of the active ingredients, i.e., the molecule(s). Such pharmaceutically acceptable buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "diluent" is intended to mean an aqueous or non-aqueous solution with the purpose of diluting the peptide in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to mean any compound added to the formulation to increase the biological effect of the peptide. The adjuvant may be one or more of zinc, copper or silver salts with different anions, for example, but not limited to fluoride, chloride, bromide, iodide, tiocyanate, sulfite, hydroxide, phosphate, carbonate, lactate, glycolate, citrate, borate, tartrate, and acetates of different acyl composition.

The excipient may be one or more of carbohydrates, polymers, lipids and minerals. Examples of carbohydrates include lactose, sucrose, mannitol, and cyclo-dextrines, which are added to the composition, e.g., for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethylene-oxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The invented formulation may also contain one or more mono- or disaccharides such as xylitol, sorbitol, mannitol, lactitiol, isomalt, maltitol or xylosides, and/or monoacylglycerols, such as monolaurin. The characteristics of the carrier are dependent on the route of administration. One route of administration is topical administration. For example, for topical administrations, a preferred carrier is an emulsified cream comprising the active peptide, but other common carriers such as certain petrolatum/mineral-based and vegetable-based ointments can be used, as well as polymer gels, liquid crystalline phases and microemulsions.

The compositions may comprise one or more molecules, such as 1, 2, 3 or 4 different molecules in the pharmaceutical compositions. In one example the invention relates to an antimicrobial composition which may be used to inhibit, prevent or destroy bacteria, both Gram positive and Gram-negative bacteria such as *Enterococcus faecalis, Escherichia coli, Pseudomonas aeruginosa, Proteus mirabilis, Streptococcus pneumoniae, Streptococcus pyogenes, Staphylococcus aureus, Finegoldia magna*, viruses, parasites, fungus and yeast, such as *Candida albicans* and *Candida parapsilosi* as well as *Malassezia* species. By using a combination of different molecules the effect may be increased and/or the possibility that the microorganism might be resistant and/or tolerant against the antimicrobial agent. However, in most cases one molecule/peptide is more suitable due to the regulatory process. The compositions may also be used to prevent/reduce or treat a disorder or disease being caused by a mixture of one or more different microorganisms, such as a mixture of different bacteria, different virus etc or a mixture of virus, bacteria, fungus, yeast and protozoans etc.

The molecule/peptide as a salt may be an acid adduct with inorganic acids, such as hydrochloric acid, sulfuric acid, nitric acid, hydrobromic acid, phosphoric acid, perchloric acid, thiocyanic acid, boric acid etc. or with organic acid such as formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalene-sulfonic acid, sulfanilic acid etc. Inorganic salts such as monovalent sodium, potassium or divalent zinc, magnesium, copper calcium, all with a corresponding anion, may be added to improve the biological activity of the antimicrobial composition.

The pharmaceutical compositions of the invention may also be in the form of a liposome, in which the peptide is combined, in addition to other pharmaceutically acceptable carriers, with amphipathic agents such as lipids, which exist in aggregated forms as micelles, insoluble monolayers and liquid crystals. Suitable lipids for liposomal formulation include, without limitation, monoglycerides, diglycerides, sulfatides, lysolecithin, phospholipids, saponin, bile acids, and the like. Preparation of such liposomal formulations is can be found in for example U.S. Pat. No. 4,235,871.

The pharmaceutical compositions of the invention may also be in the form of biodegradable microspheres. Aliphatic polyesters, such as poly(lactic acid) (PLA), poly(glycolic acid) (PGA), copolymers of PLA and PGA (PLGA) or poly (carprolactone) (PCL), and polyanhydrides have been widely used as biodegradable polymers in the production of microsheres. Preparations of such microspheres can be found in U.S. Pat. No. 5,851,451 and in EP0213303.

The pharmaceutical compositions of the invention may also be in the form of polymer gels, where polymers such as starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone are used for thickening of the solution containing the peptide.

The pharmaceutical composition may contain one or more essential oils, such as the terpenes. One example being the sesquiterpenes and farnesol.

Alternatively, the molecules may be dissolved in saline, water, polyethylene glycol, propylene glycol, ethanol or oils (such as safflower oil, corn oil, peanut oil, cottonseed oil or sesame oil), tragacanth gum, and/or various buffers. The pharmaceutical composition may also include ions and a defined pH for potentiation of action of molecules.

The pharmaceutical compositions may be subjected to conventional pharmaceutical operations such as sterilisation and/or may contain conventional adjuvants such as preservatives, stabilisers, wetting agents, emulsifiers, buffers, fillers, etc., e.g., as disclosed elsewhere herein.

The pharmaceutical compositions according to the invention may be administered locally or systemically. Routes of administration include topical, ocular, nasal, pulmonary, buccal, parenteral (intravenous, subcutaneous, and intramuscular, etc), ear, oral, vaginal, instillation (for example urinary tract etc) and rectal. Also administration from implants is possible. Suitable antimicrobial preparation forms are, for example granules, powders, tablets, coated tablets, (micro) capsules, suppositories, syrups, vagitories, emulsions, microemulsions, defined as optically isotropic thermodynamically stable systems consisting of water, oil and surfactant, liquid crystalline phases, defined as systems characterised by long-range order but short-range disorder (examples include lamellar, hexagonal and cubic phases, either water- or oil continuous), or their dispersed counterparts, gels, ointments, dispersions, suspensions, creams, sprays, gargle, aerosols, droples or injectable solution in ampule form and also preparations with protracted release of active compounds, in whose preparation excipients, diluents, adjuvants or carriers are customarily used as described above. The pharmaceutical composition may also be provided in bandages, plasters or in sutures or the like.

The pharmaceutical compositions will be administered to a patient in a pharmaceutically effective dose. By "pharmaceutically effective dose" is meant a dose that is sufficient to produce the desired effects in relation to the condition for which it is administered. The exact dose is dependent on the activity of the compound, manner of administration, nature and severity of the disorder, age and body weight of the patient different doses may be needed. The administration of the dose can be carried out both by single administration in the form of an individual dose unit or else several smaller dose units and also by multiple administration of subdivided doses at specific intervals The pharmaceutical compositions of the invention may be administered alone or in combination with other therapeutic agents, such as antibiotic, antiinflammatory or antiseptic agents such as anti-bacterial agents, anti-fungicides, anti-viral agents, and anti-parasitic agents. Examples are penicillins, cephalosporins, carbacephems, cephamycins, carbapenems, monobactams, aminoglycosides, glycopeptides, quinolones, spermine, spermidine, tetracyclines, macrolides, and fluoroquinolones. Antiseptic agents include iodine, silver, copper, clorhexidine, polyhexanide and other biguanides, chitosan, acetic acid, and hydrogen peroxide. These agents may be incorporated as part of the same pharmaceutical composition or may be administered separately. The pharmaceutical compositions may also contain anti-inflammatory drugs such as steroids and macrolactam derivatives.

The present invention concerns both humans and other mammal such as horses, dogs, cats, cows, pigs, camels, among others. Thus the methods are applicable to both human therapy and veterinary applications. The objects, suitable for such a treatment may be identified by well-established hallmarks of an infection, such as fever, puls, culture of organisms, and the like. Infections that may be treated with the molecules include those caused by or due to microorganisms. Examples of microorganisms include bacteria (e.g., Gram-positive, Gram-negative), fungi, (e.g., yeast and molds), parasites (e.g., protozoans, nematodes, cestodes and trematodes), viruses, and prions and mixtures thereof. Specific organisms in these classes are well known (see for example, Davis et al., Microbiology, 3.sup.rd edition, Harper & Row, 1980). Infections include, but are not limited to, chronic skin ulcers, infected acute wounds and burn wounds, infected skin eczema, impetigo, atopic dermatitis, acne, external otitis, vaginal infections, seborrhoic dermatitis, oral infections and parodontitis, candidal intertrigo, conjunctivitis and other eye infections, and pneumonia.

Accordingly, the pharmaceutical compositions may be used for prophylactic treatment of burn wounds, after surgery and after skin trauma. The pharmaceutical composition may also be included in solutions intended for storage and treatment of external materials in contact with the human body, such as contact lenses, orthopedic implants, and catheters.

Additionally, the pharmaceutical compositions may be used for treatment of atopic dermatitis, impetigo, chronic skin ulcers, infected acute wound and burn wounds, acne, external otitis, fungal infections, pneumonia, seborrhoic dermatitis, candidal intertrigo, candidal vaginitis, oropharyngeal candidiasis, eye infections (bacterial conjunctivitis), and nasal infections (including MRSA carriage).

The pharmaceutical compositions may also be used to in cleansing solutions, such as lens disinfectants and storage solutions or used to prevent bacterial infection in association with urinary catheter use or use of central venous catheters.

Additionally, the antimicrobial compositions may be used for prevention of infection post-surgery in plasters, adhesives, sutures, or be incorporated in wound dressings.

The molecules may also be used in polymers, wet-tissue, textiles or the like to create antibacterial surfaces or cosmetics, and personal care products (soap, shampoos, tooth paste, anti-acne, suncreams, tampons, diapers, etc) may be supplemented with the pharmaceutical compositions.

The invention also relates to the use of the above defined molecule(s) and pharmaceutical compositions in medicine.

The invention also relates to the use of the above, defined molecule or a composition as defined above for the manufacture of an antimicrobial composition for the reduction and/or elimination of microorganisms to treat or prevent a microbial infection.

Finally, the invention relates to a method of treating a mammal using the above, defined pharmaceutical compositions such as a mammal having a microbial infection or suffering from allergy comprising administering to a patient a therapeutically effective amount of the pharmaceutical composition defined above.

EXAMPLES

Definition of Sequences
In order to find analogues to the described antibacterial peptides sequence patterns were defined for the specific regions. Human proteins in the Swiss-Prot protein database (www.expasy.orglsprot/) were searched using the ScanProsite search tool (www. expasy.org/tools/scanprosite/).
The ScanProsite tool allows to scan protein sequence(s) (either from UniProt Knowledgebase (Swiss-Prot/TrEMBL) or PDB or provided by the user) for the occurrence of patterns, profiles and rules (motifs) stored in the PROSITE database, or to search protein database(s) for hits by specific motif(s)
Patterns for the conserved regions were constructed according to the following syntax:
Pattern Syntax Used in the PROSITE Database:
1. The standard IUPAC one-letter codes for the amino acids are used.
2. The symbol 'x' is used for a position where any amino acid is accepted.
3. Ambiguities are indicated by listing the acceptable amino acids for a given position, between square brackets '[ ]'. For example: [ALT] stands for Ala or Leu or Thr.
4. Ambiguities are also indicated by listing between a pair of curly brackets '{ }' the amino acids that are not accepted at a given position. For example: {AM} stands for any amino acid except Ala and Met.
5. Each element in a pattern is separated from its neighbor by a '-'.
6. Repetition of an element of the pattern can be indicated by following that element with a numerical value or, if it is a gap ('x'), by a numerical range between parentheses.

Examples x(3) corresponds to x-x-x
x(2,4) corresponds to x-x or x-x-x or x-x-x-x
A(3) corresponds to A-A-A
Note: You can only use a range with 'x', i.e. A(2,4) is not a valid pattern element.
7. When a pattern is restricted to either the N- or C-terminal of a sequence, that pattern either starts with a '<' symbol or respectively ends with a '>' symbol. In some rare cases (e.g. PS00267 or PS00539), '>' can also occur inside square brackets for the C-terminal element. 'F-[GSTV]-P-R-L-[G>]' means that either 'F-[GSTV]-P-R-L-G' or 'F-[GSTV]-P-R-L>' are considered.

Example 1

Identification of the Peptide Structure of the Antimicrobial Peptides Derived from Human Proteases 70 human proteases were identified and the amino acid sequences compared to each other.

The carboxy terminus in all these proteins ends with an α-helix, which have been shown to exhibit antimicrobial activity.

The following common amino acid sequence motif was derived from the α-helices.

X(2)-[PFY]-X(2)-[AFY]-[AITV]-X-[ILV]-X(5)-W-[IL]-X(3,32)>

Limiting the comparison to covering solely eight human coagulation factors as defined below one following common amino acid sequence motif was derived

{DS}-X-[PFY]-G-[FIV]-Y-T-X-V-{C}-[AEQRY]-X-{R}-X-W-[IL]-X-{H}-X(4,24)>

TABLE 1

Carboxy terminal antimicrobial sequences from the eight human coagulation factors belonging to the peptidase S1 family found with the narrow motif.

| | | |
|---|---|---|
| sp\|P00740\|FA9_HUMAN | GkYGIWkWSRyVnWIkEktklt.......... | (SEQ ID NO: 50) |
| sp\|P00742\|FA10_HUMAN | GkYGIWkWTAyLkWIdRsmktrglpkakshapevitssplk | (SEQ ID NO: 51) |
| sp\|P03951\|FA11_HUMAN | ErPGVWnWVEyVdWIlEktqav.......... | (SEQ ID NO: 52) |
| sp\|P08709\|FA7_HUMAN | GhFGVWrWSQyIeWLqKlmrseprpgvllrapfp... | (SEQ ID NO: 53) |
| sp\|P00748\|FA12_HUMAN | NkPGVWdWAYyLaWIrEhtvs.......... | (SEQ ID NO: 54) |
| sp\|P00734\|THRB_HUMAN | GkYGFWhWFRlKkWIqKvidqfge........ | (SEQ ID NO: 55) |
| sp\|P03952\|KLKB1_HUMAN | EqPGVWkWAEyMdWIlEktqssdgkaqmqspa.. | (SEQ ID NO: 56) |
| sp\|P04070\|PROC_HUMAN | HnYGVWkWSRyLdWIhGhirdkeapqkswap... | (SEQ ID NO: 57) |

The above, defined peptides also contain a disulfide-bonded loop approximately 55 residues further amino terminal of the carboxy terminal a-helix which also display antimicrobial activity.

Comparison of all the disulfide-bonded loops revealed the following common amino acid sequence motif:

C-{P}-X(2)-{I}-X(6,16)-M-[FILMV]-C-[AV]-G

Another peptide was also identified which displayed antimicrobial activity. The peptide is shown in SEQ ID NO:9 and is derived from the human Protein C inhibitor (PCI). The peptide corresponds to the amino acid residues 283-302 of PCI.

Example 2

Antimicrobial Peptides

The peptides were synthesised by Innovagen AB, Ideon, SE-22370, Lund, Sweden. The purity (>95%) and molecular weight of these peptides was confirmed by mass spectral analysis (MALDI.TOF Voyager) (see table 2).

TABLE 2

Antimicrobial peptides used in the study.
Name and numbering according to the unprocessed precursor in the Uni-ProtKB/Swiss-Prot entry (www.expasy.org/sprot/).

| Protein | Sequence | Designation | SEQ ID NO |
|---|---|---|---|
| FA11_HUMAN aa 545-560 | CQKRYRGHKITHKMIC | CQK16 | SEQ ID NO: 58 |
| THRB_HUMAN aa 606-622 | VFRLKKWIQKVIDQFGE | VFR17 | SEQ ID NO: 1 |

TABLE 2-continued

Antimicrobial peptides used in the study.
Name and numbering according to the unprocessed precursor in the Uni-
ProtKB/Swiss-Prot entry (www.expasy.org/sprot/).

| Protein | Sequence | Designation | SEQ ID NO |
|---|---|---|---|
| THRB_HUMAN aa 454-471 | NWRENLDRDIALMKLKKP | NWR18 | SEQ ID NO: 60 |
| FA9_HUMAN aa 439-461 | GKYGIYTKVSRYVNWIKEKTKLT | GKY23 | SEQ ID NO: 61 |
| IPSP_HUMAN aa 283-302 | SEKTLRKWLKMFKKRQLELY | SEK20 | SEQ ID NO: 62 |
| THRB_HUMANaa 598-622 | GKYGFYTHVFRLKKWIQKVIDQFGE | GKY25 | SEQ ID NO: 63 |
| FA11_HUMANaa 603-625 | ERPGVYTNVVEYVDWILEKTQAV | ERP23 | SEQ ID NO: 64 |
| KLKB1 HUMANaa 606-630 | EQPGVYTKVAEYMDWILEKTQSSDG | EQP25 | SEQ ID NO: 65 |
| THRB_HUMANaa 605-622 | HVFRLKKWIQKVIDQFGE | HVF18 | SEQ ID NO: 66 |
| FA11_HUMANaa 610-625 | NVVEYVDWILEKTQAV | NVV16 | SEQ ID NO: 67 |
| KLKB1 HUMAN aa 613-630 | KVAEYMDWILEKTQSSDG | KVA18 | SEQ ID NO: 68 |
| FA9_HUMANaa 446-461 | KVSRYVNWIKEKTKLT | KVS16 | SEQ ID NO: 69 |
| THRB_HUMAN aa 536-550 | CKDSTRIRITDNMFC | CKD15L | SEQ ID NO: 70 |
| HGF_HUMAN aa 701-725 | NRPGIFVRVAYYAKWIHKIILTYKV | NRP25 | SEQ ID NO: 71 |
| HGF_HUMAN aa 708-725 | RVAYYAKWIHKIILTYKV | RVA18 | SEQ ID NO: 72 |
| FAL39_HUMAN aa 134-170 | LLGDFFRKSKEKIGKEFKRIVQRIKDFLRNLVPRTES | LL-37 | SEQ ID NO: 59 |

The antimicrobial peptide LL-37 was included as comparison in EXAMPLE 3-6. LL-37 has a broad-spectrum antimicrobial activity against a variety of Gram-positive and Gram-negative bacterial, fungal, and viral pathogens (Niyonsaba, F. and Ogawa, H., 2005, J. Derm. Sci., 40, 157-168.). It is derived from human cationic antibacterial protein of 18 kDa (hCAP18) belonging to the cathelicidin family. The mature antibacterial peptide LL-37 is liberated through cleavage by elastase and proteinase 3 (Sorensen O. E. et al., 2001, Blood 97, 3951-3959). In addition to the peptides mentioned in the table above a larger peptide containing 35 amino acid residues and being derived from THRB HUMAN (VSWGEGCDRDGKYGFYTHVFR-LKKWIQKVIDQFGE, SEQ ID NO:49) was examined and found to have antimicrobial effect as well as the other ones.

Based on the results presented below, VFR17 was chosen for further studies. 46 new peptides (SEQ ID NO:3-48), which are based on the sequence of VFR17, were synthesized as described above. In silico evaluations seem to suggest that the 10 first amino acids (VFRLKKWIQK, SEQ ID NO:2) of SEQ ID NO:1 are important for the activity. These peptides are shown in table 2A. Their antibacterial and haemolytic effect, determined as described below, is also shown.

TABLE 2A

| | | Bacteria | | | | Erythro- | |
|---|---|---|---|---|---|---|---|
| | | E.coli ATCC 25922 | | S.aureus ATCC 29213 | | cytes Hemolysis (%) | |
| Sequence of | Sequence ID | Mean | SD | Mean | SD | Mean | SD |
| VFRLKKWIQKVIDQFGE | SEQ ID NO:1 | 9.76 | 0.85 | 6.08 | 0.72 | 9.15 | 0.74 |
| THVFRLKKWIQKVIDQFGE | SEQ ID NO:3 | 8.30 | 0.48 | 5.70 | 0.25 | 3.15 | 0.88 |
| NHVFRLKKWIQKVIDQFGE | SEQ ID NO:4 | 6.79 | 0.63 | 4.89 | 0.22 | 14.67 | 1.03 |
| SHVFRLKKWIQKVIDQFGE | SEQ ID NO:5 | 10.68 | 1.02 | 5.85 | 0.57 | 4.27 | 0.59 |
| THVFRLKKWIKKVIKQFGE | SEQ ID NO:6 | 11.27 | 0.86 | 8.16 | 0.67 | 3.62 | 0.40 |
| VFRLKKWIQKVIDQFG | SEQ ID NO:7 | 11.14 | 0.70 | 8.30 | 0.17 | 7.21 | 0.35 |
| VFRLKKWIRKVTRQFG | SEQ ID NO:8 | 11.06 | 0.47 | 6.78 | 0.40 | 3.09 | 0.07 |
| LFRLKKWIRKVTRLFG | SEQ ID NO:9 | 11.03 | 0.46 | 8.59 | 0.13 | 21.18 | 1.48 |
| LFRLKKWLRKVTKQFG | SEQ ID NO:10 | 11.00 | 1.07 | 6.28 | 0.38 | 3.95 | 0.74 |

TABLE 2A-continued

| | | Bacteria | | | | Erythrocytes Hemolysis (%) | |
| --- | --- | --- | --- | --- | --- | --- | --- |
| | | *E.coli* ATCC 25922 | | *S.aureus* ATCC 29213 | | | |
| Sequence of | Sequence ID | Mean | SD | Mean | SD | Mean | SD |
| LTRLKKWIRKVTKQFGE | SEQ ID NO:11 | 8.64 | 0.57 | 5.31 | 0.48 | 2.39 | 0.21 |
| LTRLKKWLRKVTDQFGE | SEQ ID NO:12 | 6.04 | 0.68 | 3.45 | 0.47 | 1.90 | 0.29 |
| LFRLKKWIRKVTRQFGR | SEQ ID NO:13 | 9.03 | 0.18 | 5.49 | 0.17 | 6.89 | 1.44 |
| LFRLKKWIRKVTKQFGR | SEQ ID NO:14 | 8.22 | 0.19 | 4.81 | 0.50 | 7.72 | 0.66 |
| LFRLKKWIRKVIRQFGE | SEQ ID NO:15 | 8.82 | 0.16 | 6.99 | 0.21 | 32.38 | 4.15 |
| LFR1KKWIRKVTRQFGE | SEQ ID NO:16 | 9.44 | 0.52 | 5.70 | 0.30 | 4.51 | 0.50 |
| LFRLKKWLRKVTDQFGR | SEQ ID NO:17 | 6.81 | 0.76 | 3.19 | 0.13 | 3.29 | 0.46 |
| LFRLKKWIRKVTDQFGR | SEQ ID NO:18 | 8.18 | 0.52 | 5.64 | 0.32 | 2.81 | 0.80 |
| LFRLKKWIRKVIKQFGE | SEQ TD NO:19 | 9.54 | 0.43 | 7.66 | 0.22 | 30.15 | 1.88 |
| LFRLKKWLRKVIKQFGE | SEQ ID NO:20 | 9.11 | 0.15 | 7.83 | 0.22 | 31.60 | 1.17 |
| VFRLKKWIRKVTRQFGE | SEQ ID NO:21 | 9.22 | 0.62 | 6.24 | 0.43 | 2.84 | 0.20 |
| LFRLKKWIRKVTKQFGE | SEQ ID NO:22 | 7.76 | 0.65 | 7.28 | 0.62 | 2.92 | 0.27 |
| VFRLKKWLRKVTRQFGE | SEQ ID NO:23 | 8.80 | 0.52 | 7.73 | 0.13 | 7.68 | 1.05 |
| LFRLKKWLRKVTKQFGE | SEQ ID NO:24 | 7.97 | 0.57 | 5.87 | 0.22 | 3.52 | 0.44 |
| LFRLKKWIKKVTRQFGE | SEQ ID NO:25 | 7.82 | 0.40 | 5.01 | 0.34 | 2.66 | 0.09 |
| VFRLKKWIRKVTKQFGE | SEQ ID NO:26 | 7.78 | 0.83 | 5.42 | 0.61 | 3.00 | 0.48 |
| VFRIKKWLRKVTKQFGE | SEQ ID NO:27 | 8.81 | 0.49 | 6.45 | 0.13 | 3.00 | 1.00 |
| LFRIKKWIKKVTKQFGE | SEQ ID NO:28 | 7.43 | 0.61 | 5.47 | 0.46 | 1.97 | 0.62 |
| LFRLKKWLKKVTKQFGE | SEQ ID NO:29 | 7.59 | 0.36 | 5.55 | 0.15 | 2.12 | 0.24 |
| LFRLKKWLQKVTRQFGE | SEQ ID NO:30 | 8.24 | 0.39 | 6.71 | 0.25 | 3.39 | 1.03 |
| LFRLKKWIQKVTRQFGE | SEQ ID NO:31 | 7.70 | 0.37 | 6.52 | 0.46 | 2.35 | 0.35 |
| LFRLKKWIRKVTRLFGE | SEQ ID NO:32 | 8.42 | 0.26 | 6.28 | 0.19 | 18.51 | 2.08 |
| LFRLKKWLRKVTDQFGE | SEQ ID NO:33 | 6.02 | 0.43 | 4.90 | 0.27 | 2.10 | 0.15 |
| LFRIKKWLQKVTKQFGE | SEQ ID NO:34 | 6.65 | 0.09 | 4.75 | 0.49 | 2.21 | 0.23 |
| LFRLKKWLRKVTKLFGE | SEQ ID NO:35 | 8.42 | 0.41 | 6.69 | 0.15 | 22.27 | 3.27 |
| LFRLKKWLKKVTDQFGE | SEQ ID NO:36 | 6.04 | 0.46 | 5.80 | 0.17 | 1.94 | 0.24 |
| VFRIKKWLRKVTDQFGE | SEQ ID NO:37 | 7.05 | 0.79 | 5.29 | 0.18 | 1.88 | 0.05 |
| VFRLKKWIQKVIDQFGE | SEQ ID NO:38 | 8.37 | 0.39 | 6.80 | 0.35 | 9.20 | 1.07 |
| VKRLKKWIQKVIDQFGE | SEQ ID NO:38 | 6.92 | 0.44 | 4.94 | 0.22 | 1.93 | 0.34 |
| VFRLKKWIQKVIKQFGE | SEQ ID NQ:40 | 9.56 | 0.44 | 7.25 | 0.27 | 5.48 | 1.07 |
| VFRLKKWIQKVIDQFGK | SEQ ID NO:41 | 10.26 | 0.51 | 5.98 | 0.20 | 6.02 | 0.59 |
| VKRLKKWIQKVIKQFGK | SEQ ID NO:42 | 9.47 | 0.43 | 5.92 | 0.52 | 1.99 | 0.03 |
| VKRLKKWIQKVIKLFGK | SEQ ID NO:43 | 10.34 | 0.55 | 6.37 | 0.57 | 53.44 | 3.62 |
| VKRIKKWIKKVIKLFGK | SEQ ID NO:44 | 10.46 | 0.21 | 7.21 | 0.57 | 29.20 | 7.16 |
| VRRLKKWIQKVIRQFGR | SEQ ID NO:45 | 9.48 | 0.21 | 7.25 | 0.12 | 20.48 | 4.67 |
| VRRLKKWIQKVIRLFGR | SEQ ID NO:46 | 9.88 | 0.26 | 6.48 | 0.25 | 51.53 | 2.42 |

TABLE 2A-continued

| Sequence of | Sequence ID | Bacteria | | | | Erythrocytes Hemolysis (%) | |
|---|---|---|---|---|---|---|---|
| | | E.coli ATCC 25922 | | S.aureus ATCC 29213 | | | |
| | | Mean | SD | Mean | SD | Mean | SD |
| VKRLKKWIKKVIKIFGK | SEQ ID NO:47 | 9.03 | 0.20 | 5.21 | 0.17 | 25.02 | 2.54 |
| VRRIKKWIQKVIRIFGR | SEQ ID NO:48 | 9.86 | 0.50 | 5.06 | 0.75 | 27.94 | 15.04 |
| LL-37 | SEQ ID NO: 59 | 6.57 | 1.10 | 5.63 | 0.37 | 16.43 | 1.70 |

Microorganisms

Escherichia coli ATCC25922, Pseudomonas aeruginosa ATCC27853, Staphylococcus aureus ATCC29213, Bacillus subtilis ATCC6633 bacterial isolates, and the fungal isolate Candida albicans ATCC90028, were obtained from the Department of Bacteriology, Lund University Hospital.

Example 3

Radial Diffusion Assay

Radial diffusion assays (RDA) were performed essentially as described earlier (Lehrer, R. I., Rosenman, M., Harwig, S. S., Jackson, R. & Eisenhauer, P. (1991) Ultrasensitive assays for endogenous antimicrobial polypeptides, J Immunol Methods. 137, 167-73.). Results are shown in FIG. 1 a-e. Briefly, bacteria (E. coli, P. aeruginosa, S. aureus, B. subtilis) or fungi (C. albicans) were grown to mid-logarithmic phase in 10 ml of full-strength (3% w/v) trypticase soy broth (TSB) (Becton-Dickinson, Cockeysville, Md.). The microorganisms were washed once with 10 mM Tris, pH 7.4. $4\times10^6$ bacterial cfu or $1\times10^5$ fungal cfu was added to 5 ml of the underlay agarose gel, consisting of 0.03% (w/v) TSB, 1% (w/v) low-electroendoosmosistype (Low-EEO) agarose (Sigma, St Louise Mo.) and a final concentration of 0.02% (v/v) Tween 20 (Sigma). The underlay was poured into a Ø85 mm petri dish. After agarose solidified, 4 mm-diameter wells were punched and 6 µl of test sample was added to each well. Plates were incubated at 37° C. for 3 hours to allow diffusion of the peptides. The underlay gel was then covered with 5 ml of molten overlay (6% TSB and 1% Low-EEO agarose in dH$_2$O). Antimicrobial activity of a peptide is visualized as a clear zone around each well after 18-24 hours of incubation at 37° C. for bacteria and 28° C. for Candida albicans.

Example 4

Hemolysis Assay

Figure 2:
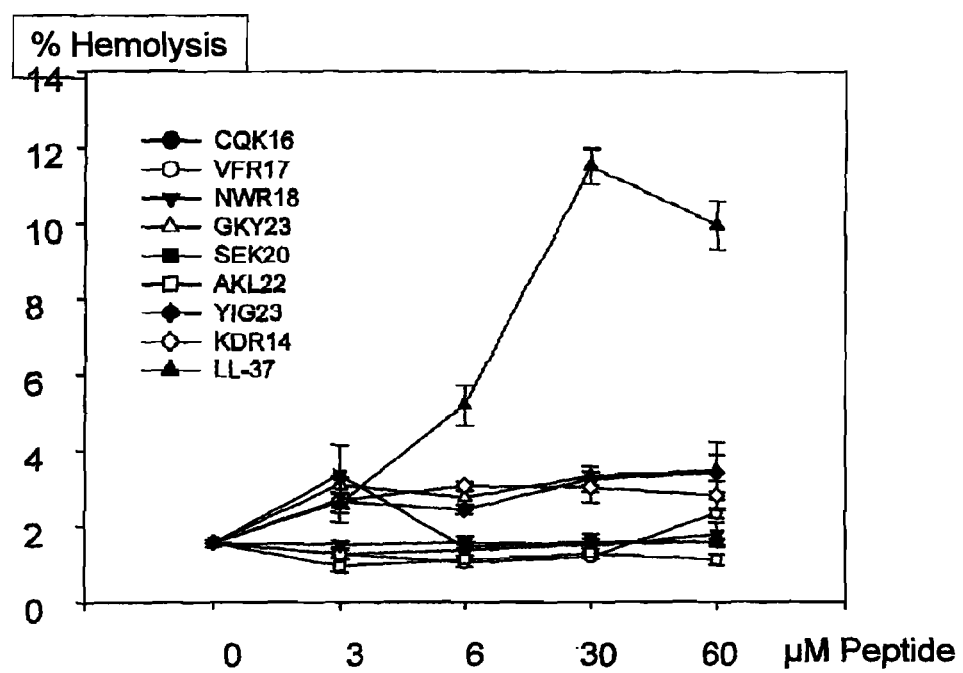
FIG. 2 Analysis of hemolytic effects of coagulation protein-derived peptides. For comparison, the human antimicrobial peptide LL-37 was included.

EDTA-blood was centrifuged at 800 g for 10 min, whereafter plasma and buffy coat were removed. The erythrocytes were washed three times and resuspended in 5% PBS, pH 7.4. The cells were then incubated with end-over-end rotation for 1 h at 37° C. in the presence of peptides (3-60 µM). 2% Triton X-100 (Sigma-Aldrich) served as positive control. The samples were then centrifuged at 800 g for 10 min. The absorbance of hemoglobin release was measured at λ 540 nm and is in the plot expressed as % of TritonX-100 induced hemolysis (FIG. 2).

Example 5

Liposome Preparation and Leakage Assay

Figure 3:
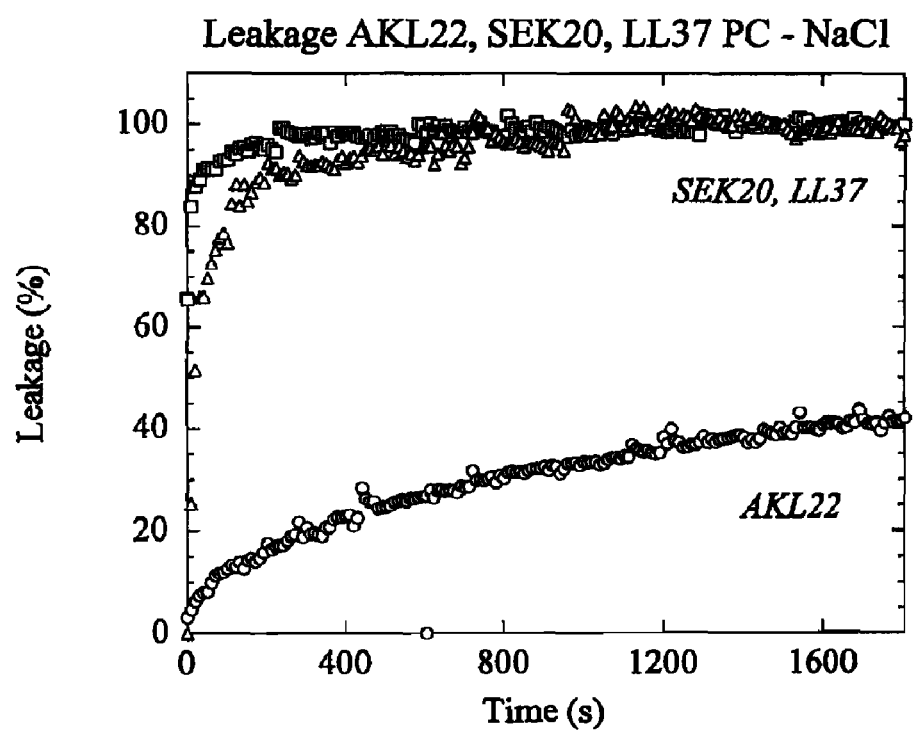
FIG. 3 CF leakage for dioleoylphosphatidylcholine/cholesterol liposomes in 10 mM Tris, pH 7.4 at 37° C. At t=0, 1 µM of peptide was added and leakage monitored by fluorescence spectroscopy. The graph shows individual runs, but the triplicate standard deviation was ±5% or less in all cases.

Dry lipid films were prepared by dissolving either dioleoylphosphatidylcholine (Avanti Polar Lipids, Alabaster, Ala.) (60 mol %) and cholesterol (Sigma, St Louis, Mo.) (40 mol %), or dioleoylphosphatidylcholine (30 mol %), dioleoylphosphatidic acid (Avanti Polar Lipids, Alabaster, Ala.) (30 mol %) and cholesterol (40 mol %) in chloroform, and then removing the solvent by evaporation under vacuum overnight. Subsequently, buffer solution containing 10 mM Tris, pH 7.4, either with or without additional 150 mM NaCl, was added together with 0.1 M carboxyfluorescein (CF) (Sigma, St Louis, Mo.). After hydration, the lipid mixture was subjected to eight freeze-thaw cycles consisting of freezing in liquid nitrogen and heating to 60° C. Unilamellar liposomes with a diameter of about 130 nm (as found with cryo-TEM; results not shown) were generated by multiple extrusions through polycarbonate filters (pore size 100 nm) mounted in a LipoFast miniextruder (Avestin, Ottawa, Canada). Untrapped carboxyfluorescein was then removed by filtration through two subsequent Sephadex G-50 columns with the relevant Tris buffer as eluent. Both extrusion and filtration was performed at 22° C. In the liposome leakage assay, the well known self-quenching of CF was used. Thus, at 100 mM CF is self-quenched, and the recorded fluorescence intensity from liposomes with entrapped CF is low. On leakage from the liposomes, released CF is dequenched, and hence fluoresces. The CF release was determined by monitoring the emitted fluorescence at 520 nm from a liposome dispersion, (10 mM lipid in 10 mM Tris pH 7.4). An absolute leakage scale is obtained by disrupting the liposomes at the end of the experiment through addition of 0.8 mM Triton X100 (Sigma, St Louis, Mo.), thereby causing 100% release and dequenching of CF. A SPEX-fluorolog 1650 0.22-m double spectrometer (SPEX Industries, Edison, N.J.) was used for the liposome leakage assay (see Table 3, FIG. 3).

TABLE 3

| SEQ ID NO | Peptide | PC − NaCl | PC + NaCl | PA − NaCl | PA + NaCl |
|---|---|---|---|---|---|
| SEQ ID NO: 58 | CQK16 | 64 ± 3 | 14 ± 4 | 18 ± 5 | 15 ± 2 |
| SEQ ID NO: 1 | VFR17 | 96 ± 3 | 18 ± 2 | 109 ± 7 | 19 ± 6 |
| SEQ ID NO: 60 | NVR18 | 4 ± 1 | 0 ± 1 | 2 ± 1 | 0 ± 1 |
| SEQ ID NO: 61 | GKY23 | 86 ± 7 | 19 ± 1 | 86 ± 4 | 30 ± 5 |
| SEQ ID NO: 62 | SEK20 | 98 ± 2 | 17 ± 5 | 64 ± 2 | 16 ± 1 |
| SEQ ID NO: 59 | LL-37 | 100 ± 10 | 73 ± 7 | 100 ± 10 | 57 ± 6 |

Example 6

CD-Spectroscopy

The CD spectra of the peptides in solution were measured on a Jasco J-810 Spectropolarimeter (Jasco, U.K.). The measurements were performed at 37° C. in a 10 mm quartz cuvet under stirring and the peptide concentration was 10 µM. The effect of on peptide secondary structure of liposomes at a lipid concentration of 100 µM was monitored in the range 200-250 nm. The only peptide conformations observed under the conditions investigated were α-helix and random coil. The fraction of the peptide in α-helical conformation, $X_\alpha$, is calculated from $$X_\alpha = (A - A_c)/(A_\alpha - A_c) \quad (1)$$

where $A$ is the recorded CD signal at 225 nm, and $A_\alpha$ and $A_c$ are the CD signal at 225 nm for a reference peptide in 100% α-helix and 100% random coil conformation, respectively. 100% α-helix and 100% random coil references were obtained from 0.133 mM (monomer concentration) poly-L-lysine in 0.1 M NaOH and 0.1 M HCl, respectively. To account for the instrumental differences between measurements the background value (detected at 250 nm, where no peptide signal is present) was subtracted. Signals from the bulk solution were also corrected for (see Table 4).

TABLE 4

Helical content (in %, in 10 mM Tris, pH 7.4) in buffer and in liposome dispersion, of peptides derived from proteins of the coagulation cascade. The antimicrobial peptide LL-37 is included for comparison.

| SEQ ID NO | Peptide | Buffer | PC | PA |
|---|---|---|---|---|
| SEQ ID NO: 58 | CQK16 | 10 ± 2 | 10 ± 2 | 8 ± 2 |
| SEQ ID NO: 1 | VFR17 | 10 ± 2 | 11 ± 2 | 38 ± 4 |
| SEQ ID NO: 61 | GKY23 | 7 ± 2 | 21 ± 2 | 29 ± 2 |
| SEQ ID NO: 62 | SEK20 | 14 ± 2 | 34 ± 4 | 38 ± 4 |
| SEQ ID NO: 59 | LL-37 | 60 ± 10 | 100 ± 10 | 100 ± 10 |

Example 7

The peptides in table 2A (SEQ ID NO: 3-48) were evaluated as described above. The data is shown in table 2A.

Example 8

The peptides with SEQ ID NO:3-10 shown in Table 2A were added in an effectiv/g cream to 2 different creams.

Cream 1; 1 g cream containing: Glycerol 200 mg, hydrogenated rape oil, cholesterol, glycerol monostearate, macro gol stearate, cetostearyl alcohol, dimethicon, liquid paraffin, solid paraffin, vaseline, propyl- and methylparahydroxybenzoate and purified water.

Cream 2; 1 g cream containing: Propylenglycol 200 mg, lactic acid 45 mg, cetostearyl alcohol, makrogol 25 cetostearylether, liquid paraffin, white vaseline, wterfree citric acid, waterfree sodium citrate, preservative (methylparahydroxybensoats E 218) and purified water.

The creams was applied to a mammal suffering from a condition similar to atopic dermatitis and found to have effect.

Example 9

The same peptides as in example 8 were dissolved in water and sprayed onto plasters. The plasters were air-dried.

What is claimed is:

1. A molecule comprising at least the amino acid sequence $X_1$-$X_2$-$X_3$-$X_4$$X_5$-$X_6$-$X_7$-$X_8$-$X_9$-$X_{10}$, wherein
   $X_1$ is V, L or I;
   $X_2$ is F, K or T;
   $X_3$ is R;
   $X_4$ is L;
   $X_5$ is K;
   $X_6$ is K;
   $X_7$ is W;
   $X_8$ is I or L;
   $X_9$ is Q, R or K; and
   $X_{10}$ is K;
wherein said molecule has a length of from 10 to 35 amino acid residues, and wherein said amino acid sequence is not SEQ ID NO:2.

2. The molecule according to claim 1, wherein at least one of the following is satisfied: $X_1$ is L; $X_2$ is K; $X_8$ is L; $X_9$ is R; or $X_9$ is K.

3. The molecule according to claim 1, comprising at least the amino acid sequence $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$, wherein
   $X_1$ is V, L or I;
   $X_2$ is F, K or T;
   $X_3$ is R;
   $X_4$ is L;
   $X_5$ is K;
   $X_6$ is K;
   $X_7$ is W;
   $X_8$ is I or L;
   $X_9$ is Q, R or K;
   $X_{10}$ is K;
   $X_{11}$ is V;
   $X_{12}$ is I or T;
   $X_{13}$ is D, K or R;
   $X_{14}$ is Q, L or I;
   $X_{15}$ is F;
   $X_{16}$ is G; and
   $X_{17}$ is E, K, R or X,
wherein the molecule has a length of from 17 to 35 amino acid residues, and wherein said amino acid sequence is not SEQ ID NO:1.

4. The molecule according to claim 3, wherein at least one of the following is satisfied: $X_1$ is L; $X_2$ is K; $X_8$ is L; $X_9$ is R or K; $X_{12}$ is T; $X_{13}$ is K or R; or $X_{17}$ is K or R.

5. The molecule according to claim 1 wherein said molecule has a length of 10, 11, 12, 13, 14, 15, 16, 17, 18, 19, 20, 21, 22, 23, 24, 25, 26, 27, 28, 29, 30, 31, 32, 33, 34 or 35 amino acid residues.

6. The molecule according to claim 1, wherein said molecule differs from SEQ ID NO:2 by the substitution of 1, 2, 3, 4, 5 or 6 amino acid residues.

7. The molecule according to claim 1, wherein the molecule is modified by amidation, esterification, acylation, acetylation, PEGylation or alkylation.

8. A composition comprising the molecule according to claim 1 and an acceptable buffer, diluent, carrier, adjuvant or excipient.

9. The composition according to claim 8 comprising one or more antibiotic and/or antiseptic agent(s) and/or anti-inflammatory agents.

10. A product comprising the molecule according to claim 1, wherein said product is selected from the group consisting of bandages, plasters, sutures, soap, tampons, diapers, shampoos, tooth paste, wet-tissues, anti-acne compounds, suncreams, textiles, adhesives, cleaning solutions or implants.

11. The composition of claim 8, wherein the composition is a medicine.

12. A method for reducing or eliminating bacterial and/or fungal microorganisms to treat and/or prevent a disease and/or disorder comprising administering to a mammal in need thereof a therapeutically effective amount of a molecule according to claim 1.

13. The method of claim 12, wherein the disease and/or disorder is selected from the group consisting of atopic dermatitis, impetigo, chronic skin ulcers, infected acute wound and burn wounds, acne, external otitis, fungal infections, pneumonia, seborrhoic dermatitis, candidal intertrigo, candidal vaginitis, oropharyngeal candidiasis, eye infections, nasal infections, after surgery or after skin trauma.

14. The method of claim 12, wherein the microorganisms are selected from the group consisting of *Enterococcus faecalis, Escherichia coli, Pseudomonas aeruginosa, Proteus mirabilis, Streptococcus pneumoniae, Streptococcus pyogenes, Staphylococcus aureus, Finegoldia magna, Candida albicans, Candida parapsilosi*, and species of *Malassezia*.

15. A method for reducing or eliminating bacterial and/or fungal microorganisms to treat and/or prevent a disease and/or disorder comprising administering to a mammal in need thereof a therapeutically effective amount of a molecule according to claim 2.

16. The method of claim 15, wherein the microorganisms are selected from the group consisting of *Enterococcus faecalis, Escherichia coli, Pseudomonas aeruginosa, Proteus mirabilis, Streptococcus pneumoniae, Streptococcus pyogenes, Staphylococcus aureus, Finegoldia magna, Candida albicans, Candida parapsilosi*, and species of *Malassezia*.

17. A method for reducing or eliminating bacterial and/or fungal microorganisms to treat and/or prevent a disease and/or disorder comprising administering to a mammal in need thereof a therapeutically effective amount of a molecule according to claim 3.

18. The method of claim 17, wherein the microorganisms are selected from the group consisting of *Enterococcus faecalis, Escherichia coli, Pseudomonas aeruginosa, Proteus mirabilis, Streptococcus pneumoniae, Streptococcus pyogenes, Staphylococcus aureus, Finegoldia magna, Candida albicans, Candida parapsilosi*, and species of *Malassezia*.

19. A method for reducing or eliminating bacterial and/or fungal microorganisms to treat and/or prevent a disease and/or disorder comprising administering to a mammal in need thereof a therapeutically effective amount of a molecule according to claim 4.

20. A molecule comprising a sequence selected from the group consisting of SEQ ID NO:3, SEQ ID NO:4, SEQ ID NO:5, SEQ ID NO:6, SEQ ID NO:7, SEQ ID NO:8, SEQ ID NO:9 and SEQ ID NO:10,
wherein the molecule has a length of from up to 35 amino acid residues.

* * * * *

SEQUENCE LISTING

<160> NUMBER OF SEQ ID NOS: 72

<210> SEQ ID NO 1
<211> LENGTH: 17
<212> TYPE: PRT
<213> ORGANISM: Artificial
<220> FEATURE:
<223> OTHER INFORMATION: synthetical peptides

<400> SEQUENCE: 1

Val Phe Arg Leu Lys Lys Trp Ile Gln Lys Val Ile Asp Gln Phe Gly
1               5                   10                  15

Glu

<210> SEQ ID NO 2
<211> LENGTH: 10
<212> TYPE: PRT
<213> ORGANISM: Artificial
<220> FEATURE:
<223> OTHER INFORMATION: synthetical peptides

<400> SEQUENCE: 2

Val Phe Arg Leu Lys Lys Trp Ile Gln Lys
1               5                   10

<210> SEQ ID NO 3
<211> LENGTH: 19
<212> TYPE: PRT
<213> ORGANISM: Artificial
<220> FEATURE:
<223> OTHER INFORMATION: synthetical peptides

<400> SEQUENCE: 3

Thr His Val Phe Arg Leu Lys Lys Trp Ile Gln Lys Val Ile Asp Gln
1               5                   10                  15

Phe Gly Glu

```
<210> SEQ ID NO 4
<211> LENGTH: 19
<212> TYPE: PRT
<213> ORGANISM: Artificial
<220> FEATURE:
<223> OTHER INFORMATION: synthetical peptides

<400> SEQUENCE: 4

Asn His Val Phe Arg Leu Lys Lys Trp Ile Gln Lys Val Ile Asp Gln
 1               5                  10                  15

Phe Gly Glu

<210> SEQ ID NO 5
<211> LENGTH: 19
<212> TYPE: PRT
<213> ORGANISM: Artificial
<220> FEATURE:
<223> OTHER INFORMATION: synthetical peptides

<400> SEQUENCE: 5

Ser His Val Phe Arg Leu Lys Lys Trp Ile Gln Lys Val Ile Asp Gln
 1               5                  10                  15

Phe Gly Glu

<210> SEQ ID NO 6
<211> LENGTH: 19
<212> TYPE: PRT
<213> ORGANISM: Artificial
<220> FEATURE:
<223> OTHER INFORMATION: synthetical peptides

<400> SEQUENCE: 6

Thr His Val Phe Arg Leu Lys Lys Trp Ile Lys Lys Val Ile Lys Gln
 1               5                  10                  15

Phe Gly Glu

<210> SEQ ID NO 7
<211> LENGTH: 16
<212> TYPE: PRT
<213> ORGANISM: Artificial
<220> FEATURE:
<223> OTHER INFORMATION: synthetical peptides

<400> SEQUENCE: 7

Val Phe Arg Leu Lys Lys Trp Ile Gln Lys Val Ile Asp Gln Phe Gly
 1               5                  10                  15

<210> SEQ ID NO 8
<211> LENGTH: 16
<212> TYPE: PRT
<213> ORGANISM: Artificial
<220> FEATURE:
<223> OTHER INFORMATION: synthetical peptides

<400> SEQUENCE: 8

Val Phe Arg Leu Lys Lys Trp Ile Arg Lys Val Thr Arg Gln Phe Gly
 1               5                  10                  15

<210> SEQ ID NO 9
<211> LENGTH: 16
<212> TYPE: PRT
<213> ORGANISM: Artificial
<220> FEATURE:
```

<223> OTHER INFORMATION: synthetical peptides

<400> SEQUENCE: 9

Leu Phe Arg Leu Lys Lys Trp Ile Arg Lys Val Thr Arg Leu Phe Gly
1               5                   10                  15

<210> SEQ ID NO 10
<211> LENGTH: 16
<212> TYPE: PRT
<213> ORGANISM: Artificial
<220> FEATURE:
<223> OTHER INFORMATION: synthetical peptides

<400> SEQUENCE: 10

Leu Phe Arg Leu Lys Lys Trp Leu Arg Lys Val Thr Lys Gln Phe Gly
1               5                   10                  15

<210> SEQ ID NO 11
<211> LENGTH: 17
<212> TYPE: PRT
<213> ORGANISM: Artificial
<220> FEATURE:
<223> OTHER INFORMATION: synthetical peptides

<400> SEQUENCE: 11

Leu Thr Arg Leu Lys Lys Trp Ile Arg Lys Val Thr Lys Gln Phe Gly
1               5                   10                  15

Glu

<210> SEQ ID NO 12
<211> LENGTH: 17
<212> TYPE: PRT
<213> ORGANISM: Artificial
<220> FEATURE:
<223> OTHER INFORMATION: synthetical peptides

<400> SEQUENCE: 12

Leu Thr Arg Leu Lys Lys Trp Leu Arg Lys Val Thr Asp Gln Phe Gly
1               5                   10                  15

Glu

<210> SEQ ID NO 13
<211> LENGTH: 17
<212> TYPE: PRT
<213> ORGANISM: Artificial
<220> FEATURE:
<223> OTHER INFORMATION: synthetical peptides

<400> SEQUENCE: 13

Leu Phe Arg Leu Lys Lys Trp Ile Arg Lys Val Thr Arg Gln Phe Gly
1               5                   10                  15

Arg

<210> SEQ ID NO 14
<211> LENGTH: 17
<212> TYPE: PRT
<213> ORGANISM: Artificial
<220> FEATURE:
<223> OTHER INFORMATION: synthetical peptides

<400> SEQUENCE: 14

Leu Phe Arg Leu Lys Lys Trp Ile Arg Lys Val Thr Lys Gln Phe Gly
1               5                   10                  15

Arg

```
<210> SEQ ID NO 15
<211> LENGTH: 17
<212> TYPE: PRT
<213> ORGANISM: Artificial
<220> FEATURE:
<223> OTHER INFORMATION: synthetical peptides

<400> SEQUENCE: 15

Leu Phe Arg Leu Lys Lys Trp Ile Arg Lys Val Ile Arg Gln Phe Gly
1               5                   10                  15

Glu

<210> SEQ ID NO 16
<211> LENGTH: 17
<212> TYPE: PRT
<213> ORGANISM: Artificial
<220> FEATURE:
<223> OTHER INFORMATION: synthetical peptides

<400> SEQUENCE: 16

Leu Phe Arg Leu Lys Lys Trp Ile Arg Lys Val Thr Arg Gln Phe Gly
1               5                   10                  15

Glu

<210> SEQ ID NO 17
<211> LENGTH: 17
<212> TYPE: PRT
<213> ORGANISM: Artificial
<220> FEATURE:
<223> OTHER INFORMATION: synthetical peptides

<400> SEQUENCE: 17

Leu Phe Arg Leu Lys Lys Trp Leu Arg Lys Val Thr Asp Gln Phe Gly
1               5                   10                  15

Arg

<210> SEQ ID NO 18
<211> LENGTH: 17
<212> TYPE: PRT
<213> ORGANISM: Artificial
<220> FEATURE:
<223> OTHER INFORMATION: synthetical peptides

<400> SEQUENCE: 18

Leu Phe Arg Leu Lys Lys Trp Ile Arg Lys Val Thr Asp Gln Phe Gly
1               5                   10                  15

Arg

<210> SEQ ID NO 19
<211> LENGTH: 17
<212> TYPE: PRT
<213> ORGANISM: Artificial
<220> FEATURE:
<223> OTHER INFORMATION: synthetical peptides

<400> SEQUENCE: 19

Leu Phe Arg Leu Lys Lys Trp Ile Arg Lys Val Ile Lys Gln Phe Gly
1               5                   10                  15

Glu

<210> SEQ ID NO 20
<211> LENGTH: 17
<212> TYPE: PRT
<213> ORGANISM: Artificial
```

```
<220> FEATURE:
<223> OTHER INFORMATION: synthetical peptides

<400> SEQUENCE: 20

Leu Phe Arg Leu Lys Lys Trp Leu Arg Lys Val Ile Lys Gln Phe Gly
1               5                   10                  15

Glu

<210> SEQ ID NO 21
<211> LENGTH: 17
<212> TYPE: PRT
<213> ORGANISM: Artificial
<220> FEATURE:
<223> OTHER INFORMATION: synthetical peptides

<400> SEQUENCE: 21

Val Phe Arg Leu Lys Lys Trp Ile Arg Lys Val Thr Arg Gln Phe Gly
1               5                   10                  15

Glu

<210> SEQ ID NO 22
<211> LENGTH: 17
<212> TYPE: PRT
<213> ORGANISM: Artificial
<220> FEATURE:
<223> OTHER INFORMATION: synthetical peptides

<400> SEQUENCE: 22

Leu Phe Arg Leu Lys Lys Trp Ile Arg Lys Val Thr Lys Gln Phe Gly
1               5                   10                  15

Glu

<210> SEQ ID NO 23
<211> LENGTH: 17
<212> TYPE: PRT
<213> ORGANISM: Artificial
<220> FEATURE:
<223> OTHER INFORMATION: synthetical peptides

<400> SEQUENCE: 23

Val Phe Arg Leu Lys Lys Trp Leu Arg Lys Val Thr Arg Gln Phe Gly
1               5                   10                  15

Glu

<210> SEQ ID NO 24
<211> LENGTH: 17
<212> TYPE: PRT
<213> ORGANISM: Artificial
<220> FEATURE:
<223> OTHER INFORMATION: synthetical peptides

<400> SEQUENCE: 24

Leu Phe Arg Leu Lys Lys Trp Leu Arg Lys Val Thr Lys Gln Phe Gly
1               5                   10                  15

Glu

<210> SEQ ID NO 25
<211> LENGTH: 17
<212> TYPE: PRT
<213> ORGANISM: Artificial
<220> FEATURE:
<223> OTHER INFORMATION: synthetical peptides

<400> SEQUENCE: 25
```

Leu Phe Arg Leu Lys Lys Trp Ile Lys Lys Val Thr Arg Gln Phe Gly
1               5                   10                  15
Glu

<210> SEQ ID NO 26
<211> LENGTH: 17
<212> TYPE: PRT
<213> ORGANISM: Artificial
<220> FEATURE:
<223> OTHER INFORMATION: synthetical peptides

<400> SEQUENCE: 26

Val Phe Arg Leu Lys Lys Trp Ile Arg Lys Val Thr Lys Gln Phe Gly
1               5                   10                  15
Glu

<210> SEQ ID NO 27
<211> LENGTH: 17
<212> TYPE: PRT
<213> ORGANISM: Artificial
<220> FEATURE:
<223> OTHER INFORMATION: synthetical peptides

<400> SEQUENCE: 27

Val Phe Arg Leu Lys Lys Trp Leu Arg Lys Val Thr Lys Gln Phe Gly
1               5                   10                  15
Glu

<210> SEQ ID NO 28
<211> LENGTH: 17
<212> TYPE: PRT
<213> ORGANISM: Artificial
<220> FEATURE:
<223> OTHER INFORMATION: synthetical peptides

<400> SEQUENCE: 28

Leu Phe Arg Leu Lys Lys Trp Ile Lys Lys Val Thr Lys Gln Phe Gly
1               5                   10                  15
Glu

<210> SEQ ID NO 29
<211> LENGTH: 17
<212> TYPE: PRT
<213> ORGANISM: Artificial
<220> FEATURE:
<223> OTHER INFORMATION: synthetical peptides

<400> SEQUENCE: 29

Leu Phe Arg Leu Lys Lys Trp Leu Lys Lys Val Thr Lys Gln Phe Gly
1               5                   10                  15
Glu

<210> SEQ ID NO 30
<211> LENGTH: 17
<212> TYPE: PRT
<213> ORGANISM: Artificial
<220> FEATURE:
<223> OTHER INFORMATION: synthetical peptides

<400> SEQUENCE: 30

Leu Phe Arg Leu Lys Lys Trp Leu Gln Lys Val Thr Arg Gln Phe Gly
1               5                   10                  15
Glu

```
<210> SEQ ID NO 31
<211> LENGTH: 17
<212> TYPE: PRT
<213> ORGANISM: Artificial
<220> FEATURE:
<223> OTHER INFORMATION: synthetical peptides

<400> SEQUENCE: 31

Leu Phe Arg Leu Lys Lys Trp Ile Gln Lys Val Thr Arg Gln Phe Gly
 1               5                  10                  15

Glu

<210> SEQ ID NO 32
<211> LENGTH: 17
<212> TYPE: PRT
<213> ORGANISM: Artificial
<220> FEATURE:
<223> OTHER INFORMATION: synthetical peptides

<400> SEQUENCE: 32

Leu Phe Arg Leu Lys Lys Trp Ile Arg Lys Val Thr Arg Leu Phe Gly
 1               5                  10                  15

Glu

<210> SEQ ID NO 33
<211> LENGTH: 17
<212> TYPE: PRT
<213> ORGANISM: Artificial
<220> FEATURE:
<223> OTHER INFORMATION: synthetical peptides

<400> SEQUENCE: 33

Leu Phe Arg Leu Lys Lys Trp Leu Arg Lys Val Thr Asp Gln Phe Gly
 1               5                  10                  15

Glu

<210> SEQ ID NO 34
<211> LENGTH: 17
<212> TYPE: PRT
<213> ORGANISM: Artificial
<220> FEATURE:
<223> OTHER INFORMATION: synthetical peptides

<400> SEQUENCE: 34

Leu Phe Arg Leu Lys Lys Trp Leu Gln Lys Val Thr Lys Gln Phe Gly
 1               5                  10                  15

Glu

<210> SEQ ID NO 35
<211> LENGTH: 17
<212> TYPE: PRT
<213> ORGANISM: Artificial
<220> FEATURE:
<223> OTHER INFORMATION: synthetical peptides

<400> SEQUENCE: 35

Leu Phe Arg Leu Lys Lys Trp Leu Arg Lys Val Thr Lys Leu Phe Gly
 1               5                  10                  15

Glu

<210> SEQ ID NO 36
<211> LENGTH: 17
<212> TYPE: PRT
<213> ORGANISM: Artificial
```

```
<220> FEATURE:
<223> OTHER INFORMATION: synthetical peptides

<400> SEQUENCE: 36

Leu Phe Arg Leu Lys Lys Trp Leu Lys Lys Val Thr Asp Gln Phe Gly
1               5                   10                  15

Glu

<210> SEQ ID NO 37
<211> LENGTH: 17
<212> TYPE: PRT
<213> ORGANISM: Artificial
<220> FEATURE:
<223> OTHER INFORMATION: synthetical peptides

<400> SEQUENCE: 37

Val Phe Arg Leu Lys Lys Trp Leu Arg Lys Val Thr Asp Gln Phe Gly
1               5                   10                  15

Glu

<210> SEQ ID NO 38
<211> LENGTH: 17
<212> TYPE: PRT
<213> ORGANISM: Artificial
<220> FEATURE:
<223> OTHER INFORMATION: synthetical peptides

<400> SEQUENCE: 38

Val Phe Arg Leu Lys Lys Trp Ile Gln Lys Val Ile Asp Gln Phe Gly
1               5                   10                  15

Glu

<210> SEQ ID NO 39
<211> LENGTH: 17
<212> TYPE: PRT
<213> ORGANISM: Artificial
<220> FEATURE:
<223> OTHER INFORMATION: synthetical peptides

<400> SEQUENCE: 39

Val Lys Arg Leu Lys Lys Trp Ile Gln Lys Val Ile Asp Gln Phe Gly
1               5                   10                  15

Glu

<210> SEQ ID NO 40
<211> LENGTH: 17
<212> TYPE: PRT
<213> ORGANISM: Artificial
<220> FEATURE:
<223> OTHER INFORMATION: synthetical peptides

<400> SEQUENCE: 40

Val Phe Arg Leu Lys Lys Trp Ile Gln Lys Val Ile Lys Gln Phe Gly
1               5                   10                  15

Glu

<210> SEQ ID NO 41
<211> LENGTH: 17
<212> TYPE: PRT
<213> ORGANISM: Artificial
<220> FEATURE:
<223> OTHER INFORMATION: synthetical peptides

<400> SEQUENCE: 41
```

```
Val Phe Arg Leu Lys Lys Trp Ile Gln Lys Val Ile Asp Gln Phe Gly
1               5                   10                  15

Lys
```

<210> SEQ ID NO 42
<211> LENGTH: 17
<212> TYPE: PRT
<213> ORGANISM: Artificial
<220> FEATURE:
<223> OTHER INFORMATION: synthetical peptides

<400> SEQUENCE: 42

```
Val Lys Arg Leu Lys Lys Trp Ile Gln Lys Val Ile Lys Gln Phe Gly
1               5                   10                  15

Lys
```

<210> SEQ ID NO 43
<211> LENGTH: 17
<212> TYPE: PRT
<213> ORGANISM: Artificial
<220> FEATURE:
<223> OTHER INFORMATION: synthetical peptides

<400> SEQUENCE: 43

```
Val Lys Arg Leu Lys Lys Trp Ile Gln Lys Val Ile Lys Leu Phe Gly
1               5                   10                  15

Lys
```

<210> SEQ ID NO 44
<211> LENGTH: 17
<212> TYPE: PRT
<213> ORGANISM: Artificial
<220> FEATURE:
<223> OTHER INFORMATION: synthetical peptides

<400> SEQUENCE: 44

```
Val Lys Arg Leu Lys Lys Trp Ile Lys Lys Val Ile Lys Leu Phe Gly
1               5                   10                  15

Lys
```

<210> SEQ ID NO 45
<211> LENGTH: 17
<212> TYPE: PRT
<213> ORGANISM: Artificial
<220> FEATURE:
<223> OTHER INFORMATION: synthetical peptides

<400> SEQUENCE: 45

```
Val Arg Arg Leu Lys Lys Trp Ile Gln Lys Val Ile Arg Gln Phe Gly
1               5                   10                  15

Arg
```

<210> SEQ ID NO 46
<211> LENGTH: 17
<212> TYPE: PRT
<213> ORGANISM: Artificial
<220> FEATURE:
<223> OTHER INFORMATION: synthetical peptides

<400> SEQUENCE: 46

```
Val Arg Arg Leu Lys Lys Trp Ile Gln Lys Val Ile Arg Leu Phe Gly
1               5                   10                  15

Arg
```

```
<210> SEQ ID NO 47
<211> LENGTH: 17
<212> TYPE: PRT
<213> ORGANISM: Artificial
<220> FEATURE:
<223> OTHER INFORMATION: synthetical peptides

<400> SEQUENCE: 47

Val Lys Arg Leu Lys Lys Trp Ile Lys Lys Val Ile Lys Ile Phe Gly
1               5                   10                  15

Lys

<210> SEQ ID NO 48
<211> LENGTH: 17
<212> TYPE: PRT
<213> ORGANISM: Artificial
<220> FEATURE:
<223> OTHER INFORMATION: synthetical peptides

<400> SEQUENCE: 48

Val Arg Arg Leu Lys Lys Trp Ile Gln Lys Val Ile Arg Ile Phe Gly
1               5                   10                  15

Arg

<210> SEQ ID NO 49
<211> LENGTH: 35
<212> TYPE: PRT
<213> ORGANISM: Artificial
<220> FEATURE:
<223> OTHER INFORMATION: synthetical peptides

<400> SEQUENCE: 49

Val Ser Trp Gly Glu Gly Cys Asp Arg Asp Gly Lys Tyr Gly Phe Tyr
1               5                   10                  15

Thr His Val Phe Arg Leu Lys Lys Trp Ile Gln Lys Val Ile Asp Gln
                20                  25                  30

Phe Gly Glu
        35

<210> SEQ ID NO 50
<211> LENGTH: 23
<212> TYPE: PRT
<213> ORGANISM: Homo sapiens

<400> SEQUENCE: 50

Gly Lys Tyr Gly Ile Tyr Thr Lys Val Ser Arg Tyr Val Asn Trp Ile
1               5                   10                  15

Lys Glu Lys Thr Lys Leu Thr
                20

<210> SEQ ID NO 51
<211> LENGTH: 42
<212> TYPE: PRT
<213> ORGANISM: Homo sapiens

<400> SEQUENCE: 51

Gly Lys Tyr Gly Ile Tyr Thr Lys Val Thr Ala Phe Leu Lys Trp Ile
1               5                   10                  15

Asp Arg Ser Met Lys Thr Arg Gly Leu Pro Lys Ala Lys Ser His Ala
                20                  25                  30

Pro Glu Val Ile Thr Ser Ser Pro Leu Lys
            35                  40
```

<210> SEQ ID NO 52
<211> LENGTH: 23
<212> TYPE: PRT
<213> ORGANISM: Homo sapiens

<400> SEQUENCE: 52

Glu Arg Pro Gly Val Tyr Thr Asn Val Val Glu Tyr Val Asp Trp Ile
1               5                   10                  15

Leu Glu Lys Thr Gln Ala Val
            20

<210> SEQ ID NO 53
<211> LENGTH: 35
<212> TYPE: PRT
<213> ORGANISM: Homo sapiens

<400> SEQUENCE: 53

Gly His Phe Gly Val Tyr Thr Arg Val Ser Gln Tyr Ile Glu Trp Leu
1               5                   10                  15

Gln Lys Leu Met Arg Ser Glu Pro Arg Pro Gly Val Leu Leu Arg Ala
            20                  25                  30

Pro Phe Pro
        35

<210> SEQ ID NO 54
<211> LENGTH: 22
<212> TYPE: PRT
<213> ORGANISM: Homo sapiens

<400> SEQUENCE: 54

Asn Lys Pro Gly Val Tyr Thr Asp Val Ala Tyr Tyr Leu Ala Trp Ile
1               5                   10                  15

Arg Glu His Thr Val Ser
            20

<210> SEQ ID NO 55
<211> LENGTH: 25
<212> TYPE: PRT
<213> ORGANISM: Homo sapiens

<400> SEQUENCE: 55

Gly Lys Tyr Gly Phe Tyr Thr His Val Phe Arg Leu Lys Lys Trp Ile
1               5                   10                  15

Gln Lys Val Ile Asp Gln Phe Gly Glu
            20                  25

<210> SEQ ID NO 56
<211> LENGTH: 33
<212> TYPE: PRT
<213> ORGANISM: Homo sapiens

<400> SEQUENCE: 56

Glu Gln Pro Gly Val Tyr Thr Lys Val Ala Gly Tyr Met Asp Trp Ile
1               5                   10                  15

Leu Glu Lys Thr Gln Ser Ser Asp Gly Lys Ala Gln Met Gln Ser Pro
            20                  25                  30

Ala

<210> SEQ ID NO 57
<211> LENGTH: 32
<212> TYPE: PRT
<213> ORGANISM: Homo sapiens

```
<400> SEQUENCE: 57

His Asn Tyr Gly Val Tyr Thr Lys Val Ser Arg Tyr Leu Asp Trp Ile
1               5                   10                  15

His Gly His Ile Arg Asp Lys Glu Ala Pro Gln Lys Ser Trp Ala Pro
            20                  25                  30

<210> SEQ ID NO 58
<211> LENGTH: 16
<212> TYPE: PRT
<213> ORGANISM: Homo sapiens

<400> SEQUENCE: 58

Cys Gln Lys Arg Tyr Arg Gly His Lys Ile Thr His Lys Met Ile Cys
1               5                   10                  15

<210> SEQ ID NO 59
<211> LENGTH: 37
<212> TYPE: PRT
<213> ORGANISM: Artificial Sequence
<220> FEATURE:
<223> OTHER INFORMATION: Consensus sequence

<400> SEQUENCE: 59

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
            35

<210> SEQ ID NO 60
<211> LENGTH: 18
<212> TYPE: PRT
<213> ORGANISM: Homo sapiens

<400> SEQUENCE: 60

Asn Trp Arg Glu Asn Leu Asp Arg Asp Ile Ala Leu Met Lys Leu Lys
1               5                   10                  15

Lys Pro

<210> SEQ ID NO 61
<211> LENGTH: 23
<212> TYPE: PRT
<213> ORGANISM: Homo sapiens

<400> SEQUENCE: 61

Gly Lys Tyr Gly Ile Tyr Thr Lys Val Ser Arg Tyr Val Asn Trp Ile
1               5                   10                  15

Lys Glu Lys Thr Lys Leu Thr
            20

<210> SEQ ID NO 62
<211> LENGTH: 20
<212> TYPE: PRT
<213> ORGANISM: Homo sapiens

<400> SEQUENCE: 62

Ser Glu Lys Thr Leu Arg Lys Trp Leu Lys Met Phe Lys Lys Arg Gln
1               5                   10                  15

Leu Glu Leu Tyr
            20
```

```
<210> SEQ ID NO 63
<211> LENGTH: 25
<212> TYPE: PRT
<213> ORGANISM: Homo sapiens

<400> SEQUENCE: 63

Gly Lys Tyr Gly Phe Tyr Thr His Val Phe Arg Leu Lys Lys Trp Ile
1               5                   10                  15

Gln Lys Val Ile Asp Gln Phe Gly Glu
            20                  25

<210> SEQ ID NO 64
<211> LENGTH: 23
<212> TYPE: PRT
<213> ORGANISM: Homo sapiens

<400> SEQUENCE: 64

Glu Arg Pro Gly Val Tyr Thr Asn Val Val Glu Tyr Val Asp Trp Ile
1               5                   10                  15

Leu Glu Lys Thr Gln Ala Val
            20

<210> SEQ ID NO 65
<211> LENGTH: 25
<212> TYPE: PRT
<213> ORGANISM: Homo sapiens

<400> SEQUENCE: 65

Glu Gln Pro Gly Val Tyr Thr Lys Val Ala Glu Tyr Met Asp Trp Ile
1               5                   10                  15

Leu Glu Lys Thr Gln Ser Ser Asp Gly
            20                  25

<210> SEQ ID NO 66
<211> LENGTH: 18
<212> TYPE: PRT
<213> ORGANISM: Homo sapiens

<400> SEQUENCE: 66

His Val Phe Arg Leu Lys Lys Trp Ile Gln Lys Val Ile Asp Gln Phe
1               5                   10                  15

Gly Glu

<210> SEQ ID NO 67
<211> LENGTH: 16
<212> TYPE: PRT
<213> ORGANISM: Homo sapiens

<400> SEQUENCE: 67

Asn Val Val Glu Tyr Val Asp Trp Ile Leu Glu Lys Thr Gln Ala Val
1               5                   10                  15

<210> SEQ ID NO 68
<211> LENGTH: 18
<212> TYPE: PRT
<213> ORGANISM: Homo sapiens

<400> SEQUENCE: 68

Lys Val Ala Glu Tyr Met Asp Trp Ile Leu Glu Lys Thr Gln Ser Ser
1               5                   10                  15

Asp Gly
```

```
-continued

<210> SEQ ID NO 69
<211> LENGTH: 16
<212> TYPE: PRT
<213> ORGANISM: Homo sapiens

<400> SEQUENCE: 69

Lys Val Ser Arg Tyr Val Asn Trp Ile Lys Glu Lys Thr Lys Leu Thr
1               5                   10                  15

<210> SEQ ID NO 70
<211> LENGTH: 15
<212> TYPE: PRT
<213> ORGANISM: Homo sapiens

<400> SEQUENCE: 70

Cys Lys Asp Ser Thr Arg Ile Arg Ile Thr Asp Asn Met Phe Cys
1               5                   10                  15

<210> SEQ ID NO 71
<211> LENGTH: 25
<212> TYPE: PRT
<213> ORGANISM: Homo sapiens

<400> SEQUENCE: 71

Asn Arg Pro Gly Ile Phe Val Arg Val Ala Tyr Tyr Ala Lys Trp Ile
1               5                   10                  15

His Lys Ile Ile Leu Thr Tyr Lys Val
            20                  25

<210> SEQ ID NO 72
<211> LENGTH: 18
<212> TYPE: PRT
<213> ORGANISM: Homo sapiens

<400> SEQUENCE: 72

Arg Val Ala Tyr Tyr Ala Lys Trp Ile His Lys Ile Ile Leu Thr Tyr
1               5                   10                  15

Lys Val
```